(12) United States Patent
Veraitch et al.

(10) Patent No.: US 12,365,858 B2
(45) Date of Patent: Jul. 22, 2025

(54) CELL PROCESSING UNIT, CELL PROCESSING SYSTEM AND METHODS OF USE THEREOF

(71) Applicant: Oribiotech LTD, London (GB)

(72) Inventors: Farlan Singh Veraitch, London (GB); Simon Collings, Datchet (GB); Nicholas Brown, Datchet (GB)

(73) Assignee: ORIBIOTECH LTD., London (GB)

( * ) Notice: Subject to any disclaimer, the term of this patent is extended or adjusted under 35 U.S.C. 154(b) by 915 days.

(21) Appl. No.: 17/419,169

(22) PCT Filed: Jan. 3, 2020

(86) PCT No.: PCT/GB2020/050007
§ 371 (c)(1),
(2) Date: Jun. 28, 2021

(87) PCT Pub. No.: WO2020/141325
PCT Pub. Date: Jul. 9, 2020

(65) Prior Publication Data
US 2022/0106550 A1    Apr. 7, 2022

(30) Foreign Application Priority Data

Jan. 4, 2019 (GB) .................................. 1900107
Jan. 4, 2019 (GB) .................................. 1900108
(Continued)

(51) Int. Cl.
*C12M 1/00* (2006.01)
*A61K 48/00* (2006.01)
(Continued)

(52) U.S. Cl.
CPC ......... *C12M 23/14* (2013.01); *A61K 48/0091* (2013.01); *C12M 23/26* (2013.01);
(Continued)

(58) Field of Classification Search
CPC .............................. C12M 23/50; C12M 23/48
See application file for complete search history.

(56) References Cited

U.S. PATENT DOCUMENTS 3,865,411 A    2/1975   Rowe et al.
4,253,500 A    3/1981   Williams
(Continued)

FOREIGN PATENT DOCUMENTS

AU    2012254908 A1    12/2012
CN       1406154 A      3/2003
(Continued)

OTHER PUBLICATIONS

Great Britain Examination Report for Great Britain Application No. 1900107.2, dated Feb. 9, 2022, 4 pages.
(Continued)

*Primary Examiner* — Nathan A Bowers
(74) *Attorney, Agent, or Firm* — TraskBritt

(57) ABSTRACT

The disclosure relates to a cell processing unit for cell and gene therapy manufacture comprising a housing defining an enclosure into which a cell processing platform can be mounted, a platform mounting bracket within the housing and configured and arranged to receive and retain a cell processing platform, a drive apparatus configured and arranged to operatively engage and act upon a cell processing platform to move same with respect to the platform mounting bracket, and an actuator configured and arranged to exert a force on a container mounted into the cell processing platform to expel a contents from the container.

20 Claims, 20 Drawing Sheets

(30) Foreign Application Priority Data

Jan. 4, 2019 (GB) ..................................... 1900109
Jan. 4, 2019 (GB) ..................................... 1900111

(51) Int. Cl.

| | |
|---|---|
| B01L 1/00 | (2006.01) |
| C12M 1/36 | (2006.01) |
| C12M 1/42 | (2006.01) |
| C12M 3/00 | (2006.01) |
| C12N 5/0783 | (2010.01) |

(52) U.S. Cl.

CPC ............ C12M 23/48 (2013.01); C12M 23/50 (2013.01); C12M 29/00 (2013.01); C12M 35/06 (2013.01); C12M 41/48 (2013.01); C12N 5/0636 (2013.01)

(56) References Cited

U.S. PATENT DOCUMENTS

| | | | |
|---|---|---|---|
| 4,717,668 A | 1/1988 | Keilman et al. | |
| 4,818,186 A | 4/1989 | Pastrone et al. | |
| 4,867,172 A | 9/1989 | Haber et al. | |
| 4,943,288 A | 7/1990 | Kurtz et al. | |
| 6,391,638 B1 | 5/2002 | Shaaltiel | |
| 6,655,655 B1 | 12/2003 | Matkovich et al. | |
| 6,656,428 B1* | 12/2003 | Clark ...................... | G01N 35/00 435/7.1 |
| 6,679,529 B2 | 1/2004 | Johnson et al. | |
| 6,880,801 B2 | 4/2005 | Matkovich et al. | |
| 7,090,191 B2 | 8/2006 | Matkovich et al. | |
| 7,284,731 B1 | 10/2007 | Johnson et al. | |
| 7,491,526 B2 | 2/2009 | Yanai et al. | |
| 8,133,165 B2 | 3/2012 | Rosiello | |
| 8,263,389 B2 | 9/2012 | Poo et al. | |
| 8,414,765 B2 | 4/2013 | Uber et al. | |
| 8,415,144 B2 | 4/2013 | Wilson et al. | |
| 9,005,181 B2 | 4/2015 | Lynn et al. | |
| 9,352,865 B2 | 5/2016 | Kuehni et al. | |
| 2003/0189349 A1 | 10/2003 | Risle et al. | |
| 2004/0149776 A1 | 8/2004 | Feygin et al. | |
| 2004/0173286 A1 | 9/2004 | Azzolini | |
| 2005/0032205 A1 | 2/2005 | Smith et al. | |
| 2005/0239199 A1 | 10/2005 | Kunas et al. | |
| 2006/0154363 A1 | 7/2006 | Horn | |
| 2007/0224676 A1 | 9/2007 | Haq | |
| 2008/0026465 A1 | 1/2008 | Nakata | |
| 2008/0118974 A1 | 5/2008 | Martin et al. | |
| 2009/0027997 A1 | 1/2009 | Meier | |
| 2010/0209298 A1 | 8/2010 | Kalra et al. | |
| 2010/0304472 A1 | 12/2010 | Kim et al. | |
| 2011/0020856 A1 | 1/2011 | Poo et al. | |
| 2011/0076756 A1 | 3/2011 | Wright | |
| 2011/0207121 A1 | 8/2011 | Chen | |
| 2011/0297275 A1 | 12/2011 | Farrar et al. | |
| 2013/0210130 A1 | 8/2013 | Larcher et al. | |
| 2014/0076454 A1 | 3/2014 | Kjar | |
| 2014/0103077 A1 | 4/2014 | Zumbrum | |
| 2014/0117824 A1 | 5/2014 | Hayami | |
| 2015/0010996 A1 | 1/2015 | Tsumura et al. | |
| 2015/0028586 A1 | 1/2015 | Gerst et al. | |
| 2015/0252317 A1 | 9/2015 | Lipkens et al. | |
| 2015/0298129 A1* | 10/2015 | Dugan ................. | B01L 3/50851 435/286.1 |
| 2015/0344161 A1 | 12/2015 | Selker et al. | |
| 2016/0152936 A1 | 6/2016 | Bargh et al. | |
| 2016/0252537 A1 | 9/2016 | Murali et al. | |
| 2016/0265022 A1 | 9/2016 | Yang-Woytowitz et al. | |
| 2016/0362653 A1 | 12/2016 | Jones et al. | |
| 2017/0079168 A1 | 3/2017 | Kawaguchi et al. | |
| 2017/0349874 A1 | 12/2017 | Jaques et al. | |
| 2018/0030398 A1 | 2/2018 | Castillo | |
| 2018/0142200 A1 | 5/2018 | Mason et al. | |
| 2018/0362910 A1 | 12/2018 | Bores et al. | |
| 2019/0022648 A1* | 1/2019 | Kim ........................ | G01N 35/10 |
| 2019/0143293 A1 | 5/2019 | Dobbyn ................... | B01J 19/28 |
| 2019/0344269 A1* | 11/2019 | Johnson .................. | B01L 7/525 |
| 2020/0190457 A1 | 6/2020 | Veraitch et al. | |
| 2021/0116470 A1* | 4/2021 | Nakayama .......... | G01N 35/1009 |
| 2022/0064580 A1 | 3/2022 | Veraitch et al. | |
| 2022/0073854 A1 | 3/2022 | Veraitch et al. | |
| 2022/0098536 A1 | 3/2022 | Veraitch et al. | |
| 2022/0098538 A1 | 3/2022 | Lundgren et al. | |
| 2023/0278026 A1* | 9/2023 | Wescott ............ | B01L 3/502715 422/67 |

FOREIGN PATENT DOCUMENTS

| | | |
|---|---|---|
| CN | 1649995 A | 8/2005 |
| CN | 101765551 A | 6/2010 |
| CN | 103255047 A | 8/2013 |
| CN | 103597065 A | 2/2014 |
| CN | 103937662 A | 7/2014 |
| CN | 104169413 A | 11/2014 |
| CN | 105392877 A | 3/2016 |
| CN | 106465573 A | 2/2017 |
| CN | 106999798 A | 8/2017 |
| CN | 107532132 A | 1/2018 |
| CN | 107636143 A | 1/2018 |
| CN | 110431222 A | 11/2019 |
| EP | 0981389 A1 | 3/2000 |
| EP | 1297861 A1 | 4/2003 |
| EP | 1909833 A2 | 4/2008 |
| EP | 2489435 A2 | 8/2012 |
| EP | 2607474 A1 | 6/2013 |
| FR | 2915488 A1 | 10/2008 |
| GB | 2507944 A | 5/2014 |
| JP | 10-146824 A | 6/1998 |
| JP | 3499790 B2 | 2/2004 |
| JP | 2004-073084 A | 3/2004 |
| JP | 2011-504748 A | 2/2011 |
| KR | 10-2018-0029366 A | 3/2018 |
| WO | 87/06952 A1 | 11/1987 |
| WO | 98/50105 A1 | 11/1998 |
| WO | 98/52631 A1 | 11/1998 |
| WO | 03/46141 | 6/2003 |
| WO | 2005/123905 A1 | 12/2005 |
| WO | 2006/122089 A2 | 11/2006 |
| WO | 2007/001915 A2 | 1/2007 |
| WO | 2008/030597 A2 | 3/2008 |
| WO | 2008/055652 A2 | 5/2008 |
| WO | 2008/073313 A2 | 6/2008 |
| WO | 2008/089510 A1 | 7/2008 |
| WO | 2010/024906 A1 | 3/2010 |
| WO | 2011/103359 A2 | 8/2011 |
| WO | 2012/173074 A2 | 12/2012 |
| WO | 2013/057500 A1 | 4/2013 |
| WO | 2013/063550 A1 | 5/2013 |
| WO | 2013/147688 A1 | 10/2013 |
| WO | 2014/042827 A2 | 3/2014 |
| WO | 2015/138489 A1 | 9/2015 |
| WO | 2016/185221 A1 | 11/2016 |
| WO | 2017/216237 A1 | 12/2017 |
| WO | 2017/220948 A1 | 12/2017 |
| WO | 2018/087558 A1 | 5/2018 |
| WO | 2019/014306 A2 | 1/2019 |

OTHER PUBLICATIONS

Great Britain Examination Report for Great Britain Application No. 1900109.8, dated Feb. 28, 2022, 4 pages.
Great Britain Search Report for Great Britain Application No. 1900107.2, dated Jul. 5, 2019, 3 pages.
Great Britain Search Report for Great Britain Application No. 1900108.0, dated Jul. 4, 2019, 4 pages.
Great Britain Search Report for Great Britain Application No. 1900109.8, dated Jul. 9, 2019, 3 pages.
Great Britain Search Report for Great Britain Application No. 1900111.4, dated Jul. 9, 2019, 3 pages.
International Search Report for International Application No. PCT/GB2020/050007, mailed Apr. 3, 2020, 4 pages.

(56) References Cited

OTHER PUBLICATIONS

International Search Report for International Application No. PCT/GB2020/050008, mailed Mar. 27, 2020, 3 pages.
International Search Report for International Application No. PCT/GB2020/050009, mailed Apr. 1, 2020, 4 pages.
International Search Report for International Application No. PCT/GB2020/050010, mailed on Mar. 27, 2020, 4 pages.
International Written Opinion for International Application No. PCT/GB2020/050007, mailed Apr. 3, 2020, 5 pages.
International Written Opinion for International Application No. PCT/GB2020/050008, mailed Mar. 27, 2020, 6 pages.
International Written Opinion for International Application No. PCT/GB2020/050009, mailed Apr. 1, 2020, 6 pages.
International Written Opinion for International Application No. PCT/GB2020/050010, mailed Mar. 27, 2020, 5 pages.
United Kingdom Patent Examination Report for United Kingdom Patent Application No. GB1900108.0, dated Jun. 14, 2023, 5 pages.
Chinese Second Office Action for Chinese Application No. 202080007625.4, dated Aug. 6, 2024, 12 pages with English translation.

* cited by examiner

CELL PROCESSING UNIT, CELL PROCESSING SYSTEM AND METHODS OF USE THEREOF

CROSS-REFERENCE TO RELATED APPLICATIONS

This application is a national phase entry under 35 U.S.C. § 371 of International Patent Application PCT/GB2020/050007, filed Jan. 3, 2020, designating the United States of America and published as International Patent Publication WO 2020/141325 A1 on Jul. 9, 2020, which claims the benefit under Article 8 of the Patent Cooperation Treaty to Great Britain Patent Application Serial No. 1900107.2 filed Jan. 4, 2019, Great Britain Patent Application Serial No. 1900108.0 filed Jan. 4, 2019, Great Britain Patent Application Serial No. 1900109.8 filed Jan. 4, 2019, and Great Britain Patent Application Serial No. 1900111.4 filed Jan. 4, 2019.

TECHNICAL FIELD

The present disclosure relates to a cell processing unit for cell and gene therapy manufacture including systems using such apparatus and methods of use thereof. The disclosure relates to methods of cell manufacture and/or gene therapy manufacture using such processing units.

BACKGROUND

Cell and gene therapy manufacturing processes are often complex and include manual or semi-automated steps across several devices. Equipment systems used in various steps (i.e., unit operations) of cell-based therapeutic products (CTP) manufacturing may include devices for cell collection, cell isolation/selection, cell expansion, cell washing and volume reduction, cell storage and transportation. The unit operations can vary immensely based on the manufacturing model (i.e., autologous versus allogenic), cell type, intended purpose, among other factors. In addition, cells are "living" entities sensitive to even the simplest manipulations (such as differences in a cell transferring procedure). The role of cell manufacturing equipment in ensuring scalability and reproducibility is an important factor for cell and gene therapy manufacturing.

In addition, cell-based therapeutic products (CTP) have gained significant momentum thus there is a need for improved cell manufacturing equipment for various cell manufacturing procedures, for example, but not limited to stem cell enrichment, generation of chimeric antigen receptor (CAR) T cells, and various cell manufacturing processes such as collection, purification, gene modification, incubation/recovery, washing, infusion into patient and/or freezing.

The culture or processing of cells typically requires the use of a device to hold the cells, for example, in an appropriate culture medium when culturing the cells. The known devices include shaker flasks, roller bottles, T-flasks and bags. Such bottles or flasks are widely used but suffer from several drawbacks. Chief among the problems are the requirement for transfer of cells without contamination when passaging or processing subsequently and the sterile addition of supplements and factors. The existing cell culture devices require re-supply of culture medium and oxygen for continued cell growth. Gas permeable cell culture devices are described in U.S. Pat. No. 8,415,144. However, such devices also require transfer of medium and/or cells in and out of the devices.

Collapsible cell processing devices for use in medicine are known: see, for example, U.S. Pat. No. 4,867,172 concerning a blood collector, or WO 2008/030597 concerning a canister liner for fluid collection. However, such devices are not fabricated or constructed for use in cell and/or gene therapy manufacturing unit operations (i.e., steps).

A key limiting factor in the production of cells or gene therapies for use in medicine is the absence of compact, automated closed systems for performing unit operations without contamination. For example, during cell culture, upstream or subsequent processing of cells, there is a risk of contamination when making additions to the culture vessel, or when removing cells or removing liquid samples. The operating systems are largely manual and hence expensive to operate. Multiple pieces of equipment are typically required to cover all of the non-cell culture steps, which involves many transfers, each of which is an opportunity for operator errors and contamination to occur. Furthermore with increasing manual operations comes increasing risk of manual errors and therefore the current labor-intensive processes lack the robustness required for the manufacture of clinical-grade therapeutics.

There is, therefore, a need for cell processing devices (e.g., multistep cell processors) that permit such processing that avoids the requirement for constant movement of cells into fresh devices. For example, it would be advantageous if scale-up of cells in culture could be achieved without transfer of cells into a larger device as the cell population for any given culture increases.

Previous cell manufacturing devices use complex equipment that is large and difficult to assemble. The devices use complex networks of tubing, valves and pumps to link elements of the equipment together.

An improved cell and/or gene therapy processing equipment is provided that combines the advantages of the cell culture containers of earlier applications (PCT/GB2016/051451 and PCT/GB2017/053389) (i.e., avoiding the need for pumps and the requirement for constant passaging of cells into fresh culture devices, holding vessels, tubes etc.) with the advantages conferred by having individually configurable cell and/or gene therapy processing devices. Together with an improved, closed cell processing unit, the improved device and container described herein permit a variety of unit processes to be performed within a single device or container having a smaller footprint and being less complex than existing equipment, as will be explained in more detail herein. Moreover, the cell processing containers described herein may maintain an aseptic connection without the prerequisite of a laminar flow cabinet, a glove box, or the like.

An earlier application (PCT/GB2016/051451) describes a cell culture container in which the wall element, being composed of a flexible material, is compressible with respect to its top and base sections. The cell culture container described therein is compatible with the cell processing unit and device described herein.

In a further earlier application (PCT/GB2017/053389) an improved version of a cell culture container is described, having at least one inlet and further comprising one or more auxiliary containers in fluid communication with the primary container. The cell culture container described therein is improved to be compatible with the cell processing unit and device described herein. Moreover, a connection between the cell culture container described therein and other components is improved, thereby maintaining an aseptic environment through the connection. In the earlier application (PCT/GB2017/053389), a laminar flow cabinet was required in order to ensure an aseptic environment during cell and/or gene therapy manufacture and/or processing. However, this can increase costs and result in a more labor-intensive process. Thus, the present disclosure also aims to provide an aseptic connection between components, irrespective of the surrounding environment or atmosphere.

BRIEF SUMMARY

It is an object of certain aspects of the present disclosure to provide an improvement over the above described techniques and known art; particularly to provide a cell processing unit, a cell processing platform, a cell processing device and a cell processing container and systems that facilitate flexible, compact, low cost, multistep cell processing while reducing the risk of contamination.

In accordance with the present disclosure there is provided a cell processing unit for cell and/or gene therapy manufacture and a cell processing system and method in accordance with the accompanying claims.

Also described is provided a platform cell processing platform for use in one or more unit operations in cell and/or gene therapy manufacture and a cell processing system and method.

Also described is a cell processing device for use in one or more unit operations in cell and/or gene therapy manufacture and a cell processing system and method.

Also described is a cell processing container for use one or more unit operations in cell and/or gene therapy manufacture, a cell processing system comprising a cell processing container and a multi-step method of performing one or more unit operations in cell and/or gene therapy manufacture.

Cell Processing Unit

According to an aspect of the disclosure there is provided a cell processing unit for cell and gene therapy manufacture comprising a housing defining an enclosure into which a cell processing platform can be mounted, a platform mounting bracket within the housing and configured and arranged to receive and retain a cell processing platform, a drive apparatus configured and arranged to operatively engage and act upon the cell processing platform to move same with respect to the platform mounting bracket, and an actuator configured and arranged to exert a force on a container mounted into the cell processing platform to expel a contents from the container.

The term "cell processing unit" is used to define a unit in which one or more unit operations in cell and/or gene therapy manufacture or processing may be performed. The cell processing unit may serve as a housing for components used in such manufacture and processing. The cell processing unit may take any suitable shape or size. The cell processing unit may take the form of an apparatus or the like. That is, the terms "cell processing unit," "cell processing apparatus" and "an apparatus for cell and/or gene therapy manufacture or processing" may be used interchangeably.

The term "enclosure" is used to define an area or space in which another component can be received, housed or enclosed, either partially or fully. The enclosure may take the form of a chamber, a receptacle, a volume of space or the like.

The term "cell processing platform" is used to define a platform, or an interface, upon which one or more unit operations in cell and/or gene therapy manufacture or processing may be performed. The terms "cell processing platform," "liquid handling platform," "platform," "cell processing interface" and "interface" can be used synonymously. In some examples, the cell processing platform serves as an interface between components, for example, containers, bioreactors or the like, such that the user can manipulate the cell processing platform thereby controlling one or more unit operations in cell and/or gene therapy manufacture or processing. The cell processing platform may provide a fluid pathway, through conduits, seals, valves, septa or the like to provide an interface between components, for example, containers, bioreactors or the like.

The term "platform mounting bracket" is used to define a mounting bracket for a cell processing platform as described herein. The platform mounting bracket may take the form of one or more components configured and arranged such that a cell processing platform may be mounted thereto.

The term "actuator" is used to define an operable mechanism that may cause actuation, or operation, of one or more components of the cell processing unit or cell processing platform. In some examples, the actuator may cause actuation, or operation, of one or more containers. In some examples, the actuator may cause actuation, or operation or compression, of one or more compressible containers. In some examples, the actuator may cause activation, or operation, of one or more valves.

In certain embodiments, the housing is accessible through a door in a wall of the housing. More specifically, the door may be hingedly connected to the wall of the housing. Yet more specifically, the door is positioned in a front wall of the housing. In this way, front loading of the cell processing unit is possible.

In certain embodiments, the housing has a rectangular or square footprint.

In certain embodiments, the platform mounting bracket comprises a mounting plate. More specifically, the mounting plate is configured to receive a portion of a cell processing platform. In this way, a cell processing platform is retained on the mounting plate when in use.

In certain embodiments, the platform mounting bracket comprises a mounting flange spaced apart from the mounting plate in order that a cell processing platform can be received and retained in position in the housing between the mounting plate and the mounting flange. More specifically, the mounting flange and the mounting plate together provide a recess (slot) into which a portion of a cell processing platform can be located and retained.

In certain embodiments, the mounting plate is substantially C-shaped. Thus, a cell processing platform can be moved into location on the mounting plate from a sideways (i.e., front) loading position.

In certain embodiments, the mounting plate is mounted to the housing.

In certain embodiments, the mounting plate is adjustable. More specifically, the distance between the base of the housing and the mounting plate is adjustable. In this way, different cell processing devices can be located in the housing.

In certain embodiments, the mounting plate is positioned within the housing to allow a cell processing device to be supported by the plate without contacting the walls, top or base of the housing. In this way, the mounting plate suspends a cell processing device in the housing.

The cell processing device is therefore able to rotate in the housing.

In certain embodiments, the drive apparatus is a rotational drive apparatus configured and arranged to operatively engage and act upon a cell processing platform to rotate the same with respect to the platform mounting bracket. Thus, the cell processing platform, once positioned in the cell processing unit and engaged with the rotational drive apparatus, can be indexed in its position relative to the platform mounting bracket by operation of the rotational drive apparatus. Thus, in certain embodiments, the cell processing unit is operable to move a cell processing platform within it in an automatic process.

In certain embodiments, the rotational drive apparatus comprises a drive wheel that is mounted on the platform mounting bracket and is configured to engage a surface of a cell processing platform and to impart rotational movement on it.

In certain embodiments, the rotational drive apparatus comprises a sprung wheel biased toward the drive wheel and spaced apart from it and mounted on the platform mounting bracket.

In certain embodiments, the rotational drive apparatus comprises a hinged wheel biased toward the drive wheel and spaced apart from it and mounted on the platform mounting bracket.

The term "hinged wheel" is used to define a wheel hingedly mounted, that is, mounted upon a hinge, such that it may be moveable between at least a first configuration and a second configuration. The wheel may be hingedly mounted in any suitable way, and may be moveable between any number of appropriate configurations.

In certain embodiments, the hinged wheel is moveable into an open position in which a cell processing platform can be inserted into and engaged with the platform mounting bracket and a closed position in which the hinged wheel is engaged with a surface of the cell processing platform in order to retain the same in the cell processing platform mounting bracket.

In certain embodiments, the hinged wheel is moveable manually.

In certain embodiments, the hinged wheel is moveable automatically. More specifically, the hinged wheel may be operatively coupled to an actuator operable to move the hinged wheel between the open position and the closed position.

In certain embodiments, the hinged wheel is mounted to the door of the housing.

In certain embodiments, the door of the housing comprises a platform engaging means. More specifically, the platform engaging means is one of: a flange, a protrusion or a lug located on the inside of the door (facing the inside of the housing) and being operable to engage with the surface of a cell processing platform when the door is closed. In this way, the platform engaging means is operable to retain the cell processing platform in the mounting bracket. The platform engaging means may also be operable to maintain the cell processing platform in engagement with the drive wheel of the rotational drive apparatus.

In certain embodiments, the drive apparatus comprises a three-point contact arrangement. In this way, a cell processing platform in the cell processing unit is retained in the drive mechanism around its full circumference.

In certain embodiments, the three elements of the drive apparatus (e.g., the drive wheel, the sprung wheel and the hinged wheel) are equally spaced from one another within the housing. Such an arrangement facilitates the rotational movement of the cell processing platform with the least number of drive wheels.

In certain embodiments, the actuator is a linear actuator.

The term "linear actuator" is used to define an actuator that moves in a linear manner, that is, along an axis. In some examples, the linear actuator may be operable along a longitudinal axis.

In certain embodiments, the actuator comprises a lever, a plunger or a series of levers, plungers or bellows configured to compress a container mounted into the cell processing platform. In certain embodiments, the actuator is configured to compress the primary container and/or the one or more auxiliary containers mounted to the cell processing platform and located in the housing.

In certain embodiments, the linear actuator comprises a plunger operatively coupled to a drive motor, wherein the plunger is configured to engage a container in the cell processing platform and to exert a compression force on the container.

In certain embodiments, the cell processing unit comprises a plurality of actuators.

In certain embodiments, the apparatus comprises a primary actuator configured and arranged to exert a force on a primary container mounted to the cell processing platform to expel a contents (e.g., a fluid, cells or the like) from the container.

In certain embodiments, the primary actuator is a linear actuator.

In certain embodiments, the linear primary actuator comprises a lever, a plunger or a series of levers, plungers or bellows configured to compress the primary container.

In certain embodiments, the primary actuator comprises a plunger operatively coupled to a drive motor, wherein the plunger is configured to engage a primary container mounted to the cell processing platform and to exert a compression force on the primary container.

It will be understood that any actuator should preferably be capable not merely of compressing or collapsing a container mounted to the cell processing platform but also of re-opening it where this is required. In this way, the contents of the container can be agitated by repeated compression/extension of the container.

In certain embodiments, the apparatus comprises a valve actuator operable to act upon a valve in the cell processing platform to open and close same as force is applied to the container. In certain embodiments, the valve is a pinch valve.

In certain embodiments, the valve actuator is a linear actuator.

In certain embodiments, the valve actuator comprises a valve solenoid.

In certain embodiments, the apparatus comprises a location detecting sensor operable to detect the position of the cell processing platform relative to the platform mounting bracket.

In certain embodiments, the location detecting sensor is operable to detect the rotational position of the cell processing platform relative to the platform mounting bracket. In this way, the location of container ports, and therefore the containers mounted in the cell processing platform, is detectable as the cell processing platform moves relative to the housing.

In certain embodiments, the location detecting sensor comprises one or more of: a Hall Effect sensor, an RFID sensor, a light sensor or a cog operable to engage a further cog.

In certain embodiments, the apparatus comprises a home location detecting sensor operable to detect a home position of the cell processing platform relative to the platform mounting bracket.

The term "home position" is used to define a first, default or original position of configuration of the cell processing platform. The home position may be referred to as so with respect to a predetermined position in relation to the platform mounting bracket.

In certain embodiments, the home location detecting sensor is operable to detect a single rotational position of the cell processing platform relative to the platform mounting bracket.

The term "a single rotational position" is used to define a position within the path of rotation of the cell processing platform. The single rotational position may be referred to as so with respect to a position on the platform mounting bracket, for example, a predetermined position.

In certain embodiments, the home location detecting sensor comprises one or more of: a Hall Effect sensor, an RFID sensor, a light sensor or a cog operable to engage a further cog.

In certain embodiments, the voltage detected by the Hall Effect sensor is greater at the home position of the cell processing platform relative to the platform mounting bracket than at any other position during the rotation of the cell processing platform relative to the platform mounting bracket.

In certain embodiments, a container is mounted to the cell processing platform to form a cell processing device as described herein. More specifically, the container is compressible. In this way, the container configuration is based on a concertina (which can act as a pump) therefore there is no need for separate pumps and complex sets of tubing/pipes to transfer the contents of a container to another container in the system. In turn this configuration reduces the space needed for a cell and/or gene therapy manufacturing process.

In certain embodiments, the container is a container described in patent application PCT/GB2016/051451.

In certain embodiments, the container is a container described in patent application PCT/GB2017/053389.

In certain embodiments, the container comprises a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material. Alternatively the container may comprise a syringe arrangement allowing it to be re-filled or emptied. In such a syringe arrangement, the container has an arrangement analogous to a syringe having an element that is moveable to either expel fluid from the container or draw it back in.

In certain embodiments, the container may comprise any shaped container with a moving seal allowing variable volume operations.

In certain embodiments, the primary container is compressible.

In certain embodiments, the primary container comprises a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

In certain embodiments, the container(s) is one of: a reagent container, a bioreactor, a cell culture container, a waste container, a filter, an electroporator, a purifier, a waste container, a filter, an electroporator, a purifier, holding container, apheresis/leukopheresis, differentiation chamber, chromatography column, settling chamber, sieve, shaking/mixer a centrifuge and a magnetic bead separator or the like.

In certain embodiments, the primary container is a cell culture container.

In certain embodiments, control of the cell processing unit is automated.

The term "automated" is used to refer to operation of a component without, or substantially without, user intervention.

In certain embodiments, the cell processing unit comprises a control system operable to activate the actuator and/or the drive means. In this way, a cell processing device loaded into the unit can be selectively moved to position a container in line with the actuator and/or the actuator activated to act upon a container in the housing to expel its contents.

In certain embodiments, the control system is manually or automatic. More specifically, the automatic control system may be programmed to operate the actuator and/or the drive means in a predetermined sequence.

In certain embodiments, the control system comprises a user interface on the housing.

In certain embodiments, the control system comprises a user interface operably linked to and remote from the housing.

In certain embodiments, the user interface is operable to allow a user to program instructions into the control system.

In certain embodiments, the cell processing unit comprises a temperature control means. In this way, the temperature within the housing can be controlled and selected.

According to another aspect the present disclosure provides a cell processing system comprising a cell processing unit according to the disclosure.

According to a yet further aspect of the present disclosure there is provided a method of cell and/or gene therapy manufacture utilizing a cell processing unit according to the present disclosure.

Cell Processing Platform

According to a further aspect of the disclosure there is provided a cell processing platform for use in performing one or more unit operations in cell and/or gene therapy manufacture, the platform comprising a body portion comprising at least one fluid inlet fluidly connected to a fluid outlet, and an auxiliary container port fluidly coupled to the at least one fluid inlet of the body portion, wherein the auxiliary container port is configured and arranged to receive and sealingly engage with an auxiliary container and to fluidly connect the auxiliary container lumen with the at least one fluid inlet of the body portion, and a primary container port configured and arranged to sealingly engage with a primary container and to fluidly connect the primary container lumen with the fluid outlet of the body portion.

The term "cell processing platform" is used to define a platform, or an interface, upon which one or more unit operations in cell and/or gene therapy manufacture or processing may be performed. The terms "cell processing platform," "liquid handling platform," "platform," "cell processing interface" and "interface" can be used synonymously. In some examples, the cell processing platform serves as an interface between components, for example, containers, bioreactors or the like, such that the user can manipulate the cell processing platform thereby controlling one or more unit operations in cell and/or gene therapy manufacture or processing. The cell processing platform may provide a fluid pathway, through conduits, seals, valves, septa or the like to provide an interface between components, for example, containers, bioreactors or the like. The cell processing platform may provide an aseptic fluid pathway through conduits, seals, valves, septa or the like to provide an interface between components, for example, containers, bioreactors or the like.

The primary container may be regarded as a first container. The auxiliary container may be regarded as a second, or a secondary, container. Any number of containers may be used.

The term "primary container" is used to define that a container is connected to a first side, or surface, of the cell processing platform. For example, the term "primary container" may be used to define that the container is attached to a lower side, or surface, of the cell processing platform. There may be any number of primary containers.

The primary container may be a bellow-based container, for example, a bellow-based bioreactor. That is, the container or bioreactor may be based on a bellows, i.e., a container or bioreactor including a wall element comprising a series of Z-folds, or a wall element comprising, or forming, a concertina. The bellow-based container or bioreactor may include a base section, a top section arranged substantially in parallel with the base section and a wall element arranged between the top section and the base section and defining an internal lumen of the container or bioreactor. The wall element of the container or bioreactor preferably is compressible with respect to the top and base sections. The wall element of the container or bioreactor may be composed of a flexible material. The wall element may comprise a series of Z-folds. The wall element may comprise, or form, a bellows. The container may take the form of a concertina.

The term "auxiliary container" or "secondary container" is used to define that a container is connected to a second side, or surface, of the cell processing platform. For example, the term "auxiliary container" or "secondary container" may be used to define that the container is attached to an upper side, or surface, of the cell processing platform. There may be any number of auxiliary containers.

The auxiliary container may be a bellow-based container, for example, a bellow-based bioreactor. That is, the container or bioreactor may be based on a bellows, i.e., a container or bioreactor including a wall element comprising a series of Z-folds, or a wall element comprising, or forming, a concertina. The bellow-based container or bioreactor may include a base section, a top section arranged substantially in parallel with the base section and a wall element arranged between the top section and the base section and defining an internal lumen of the container or bioreactor. The wall element of the container or bioreactor preferably is compressible with respect to the top and base sections. The wall element of the container or bioreactor may be composed of a flexible material. The wall element may comprise a series of Z-folds. The wall element may comprise, or form, a bellows. The container may take the form of a concertina.

Generally, the term "container," or a "cell processing container," is used to define a container, a receptacle, a volume, a bioreactor, or the like in which one or more unit operations of cell and/or gene therapy manufacture or processing may be completed.

In certain embodiments, the body portion includes one, that is, a single fluid inlet, and one, that is, a single, fluid outlet. In certain embodiments, the body portion includes one or more fluid inlets, and one or more fluid outlets. In certain embodiments, the body portion includes one, that is, a single, fluid inlet, and a plurality of fluid outlets. In certain embodiments, the body portion includes a plurality of fluid inlets, and one, that is, a single, fluid outlet. In certain embodiments, the body portions include a plurality of fluid inlets, and a plurality of fluid outlets.

In certain embodiments, the auxiliary container port comprises a sealable fluid inlet and/or a sealable fluid outlet.

In certain embodiments, the auxiliary container port is configured for sealing engagement with the fluid outlet of an auxiliary container.

In certain embodiments, the primary container port is configured for sealing engagement with the fluid inlet of a primary container.

In certain embodiments, the auxiliary container port comprises a container-receiving sleeve connected to the body portion and being configured to surround at least a portion of the auxiliary container, which portion comprises the fluid outlet of the container.

In certain embodiments, the container-receiving sleeve comprises insulation means configured to maintain the contents of an auxiliary container received in the sleeve at a particular temperature. More specifically, the insulation means is a thermal sleeve. Accordingly, the auxiliary container-receiving port may be configured to maintain the contents of a container received within the port at an optimal temperature. For example, the optimal temperature may be cell culture temperature (37 degrees Celsius), or room temperature (22 degrees Celsius), or refrigerated (e.g., around 4 degrees Celsius), or below freezing (e.g., around minus 4 degrees Celsius or lower, such as minus 20 degrees Celsius, or minus 80 degrees).

In certain embodiments, the cell processing platform may have one or more auxiliary container ports configured to maintain a variety of temperatures.

In certain embodiments, the auxiliary container port comprises a mating element configured to fluidly connect to a corresponding mating element on an auxiliary container.

In certain embodiments, the mating element is one of: a sterile connector end or a LUER-LOK™. When the mating element of the auxiliary container port is a LUER-LOK™, the port may have a male LUER-LOK™ connector that will engage and couple with a corresponding female LUER-LOK™ connector on the container or vice versa.

In certain embodiments, the primary container port comprises a mating element configured to fluidly connect to a corresponding mating element on a primary container.

In certain embodiments, the mating element comprises one of: a sterile connector end or a LUER-LOK™ When the mating element of the primary container port is a LUER-LOK™, the port may have a male LUER-LOK™ connector that will engage and couple with a corresponding female LUER-LOK™ connector on the container or vice versa.

In certain embodiments, the auxiliary container port comprises a LUER-LOK™ connector at the fluid inlet and/or the fluid outlet of the auxiliary container port, each LUER-LOK™ connector configured to engage with a further LUER-LOK™ connector on a container and/or on the body portion, respectively. More specifically, a male LUER-LOK™ connector is configured to engage with a female LUER-LOK™ connector.

In certain embodiments, the fluid outlet of the body portion comprises a LUER-LOK™ connector configured to engage with a further LUER-LOK™ connector on a primary container attachable to the body portion.

In certain embodiments, the auxiliary container port comprises a sterile connector end at the fluid inlet and/or the fluid outlet of the auxiliary container port, each sterile connector end configured to engage with a further sterile connector end on a container and/or on the body portion, respectively.

In certain embodiments, the fluid outlet of the body portion comprises a sterile connector end configured to engage with a further sterile connector end on a primary container attachable to the body portion.

In certain embodiments, the body portion is substantially hollow.

In certain embodiments, the at least one fluid inlet and the fluid outlet of the body portion are fluidly coupled to one another by a fluid conduit.

In certain embodiments, the fluid conduit comprises a valve operable to open and close the fluid conduit.

In certain embodiments, the valve is one of: a pinch valve, a pressure-sensitive valve, a clamp valve, a membrane valve, a rupture disc, a venous valve and an aperture valve.

In certain embodiments, the auxiliary container port comprises a container filling port.

In certain embodiments, the container filling port is fluidly connected to a fluid inlet of the auxiliary container port.

In certain embodiments, the container filling port comprises a valve operatively coupled to the fluid inlet and a fluid outlet of the auxiliary container port and operable to control fluid flow direction through the auxiliary container port.

In certain embodiments, the container filling port comprises a valve operable, in an open position, to allow fluid to flow to the fluid inlet of the auxiliary container port and not to the fluid outlet of the auxiliary container port and, in a closed position, to close the container filling port and to allow fluid to flow from the fluid inlet of the auxiliary container port to the fluid outlet of the auxiliary container port.

In certain embodiments, the platform comprises a plurality of auxiliary container ports each fluidly connected to a fluid inlet of the body portion. In this way, each of the plurality of auxiliary container ports is configured and arranged to receive and sealingly engage with an auxiliary container and to fluidly connect the container lumen with a fluid inlet of the body portion.

In certain embodiments, each auxiliary container port is coupled to a separate fluid inlet of the body portion.

In certain embodiments, each separate fluid inlet of the body portion is fluidly connected to a fluid outlet of the body portion.

In certain embodiments, the platform comprises at least one positional tracking device operable to indicate a set location on the platform. In this way, the position of the platform may be tracked, for example, when the platform is mounted into a cell processing unit according to the disclosure.

In certain embodiments, the at least one positional tracking device is a mechanical device.

In certain embodiments, the at least one positional tracking device comprises a cog. In such embodiments, the mounting plate of the cell processing unit may comprise a further cog operable to engage the projections of the cog on the cell processing platform. In this way, the cell processing platform will need to be physically inserted into the mounting plate of the cell processing unit in the correct orientation. This, in turn, ensures the operator knows the position of the platform and thus containers mounted to the platform in the cell processing unit.

In certain embodiments, the positional tracking device is an encoder. More specifically, the positional tracking device is one or more of: a magnet, an RFID sensor, a light sensor or the like.

In certain embodiments, the platform comprises a plurality of positional tracking devices.

In certain embodiments, the at least one positional tracking device is located relative to the (or each) auxiliary container port such that the location of the positional tracking device is related to the position of the auxiliary container port.

In certain embodiments, the at least one positional tracking device is located on the body portion relative to the auxiliary container port.

In certain embodiments, the platform comprises a sampling port in the body portion.

In certain embodiments, the platform comprises a gas transfer port in the body portion.

In certain embodiments, the auxiliary container port is configured to receive a container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

In certain embodiments, the auxiliary container port is configured to receive a container described in International Patent Application Number PCT/GB2016/051451.

In certain embodiments, the auxiliary container is detachably mounted to the auxiliary container port.

In certain embodiments, the primary container port is configured to receive a primary container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

In certain embodiments, the auxiliary container port is configured to receive a primary container described in International Patent Application Number PCT/GB2016/051451 or PCT/GB2017/053389.

In certain embodiments, the primary container further comprises an attachment flange mounted to the top section of the primary container and being configured to sealingly engage and mount to the primary container port.

In certain embodiments, the primary container is detachably mounted to the primary container port.

Cell Processing Device

According to a yet further aspect of the disclosure there is provided a cell processing device for use in performing one or more unit operations in cell and/or gene therapy manufacture comprising a cell processing platform according to the disclosure fluidly coupled to at least one container.

The term "cell processing device" is used to define a cell processing platform having at least one container coupled thereto. The at least one container may be fluidly coupled thereto.

The term "cell processing platform" is used to define a platform, or an interface, upon which one or more unit operations in cell and/or gene therapy manufacture or processing may be performed. The terms "cell processing platform," "liquid handling platform," "platform," "cell processing interface" and "interface" can be used synonymously. In some examples, the cell processing platform serves as an interface between components, for example, containers, bioreactors or the like, such that the user can manipulate the cell processing platform thereby controlling one or more unit operations in cell and/or gene therapy manufacture or processing. The cell processing platform may provide a pathway, for example, a fluid pathway, through conduits, seals, valves, septa or the like to provide an interface between components, for example, containers, bioreactors or the like.

In some examples, the cell processing platform may be fluidly coupled to at least one container thereby allowing fluid communication therebetween. That is, in some examples, the cell process platform allows the introduction or extraction of one or more fluids to or from the at least one container.

In certain embodiments, the cell processing platform is fluidly coupled to at least one auxiliary container.

In certain embodiments, the cell processing platform is fluidly coupled to at least one primary container.

Thus, in certain embodiments, there is provided a cell processing device for use in performing one or more unit operations in cell and/or gene therapy manufacture comprising a cell processing platform fluidly coupled to at least one auxiliary container and being fluidly coupled to at least one primary container.

In certain embodiments, the cell processing platform comprises a body portion comprising at least one fluid inlet fluidly connected to a fluid outlet, and an auxiliary container port fluidly coupled to the at least one fluid inlet of the body portion, wherein the at least one auxiliary container is received in sealing engagement with the auxiliary container port such that the auxiliary container lumen is fluidly connected with the at least one fluid inlet of the body portion, and a primary container is received in sealingly engagement with the primary container port such that the primary container lumen is fluidly connected with the fluid outlet of the body portion.

The primary container may be regarded as a first container. The auxiliary container may be regarded as a second, or a secondary, container. Any number of containers may be used.

The term "primary container" is used to define that a container is connected to a first side, or surface, of the cell processing platform. For example, the term "primary container" may be used to define that the container is attached to a lower side, or surface, of the cell processing platform. There may be any number of primary containers.

The primary container may be a bellow-based container, for example, a bellow-based bioreactor. That is, the container or bioreactor may be based on a bellows, i.e., a container or bioreactor including a wall element comprising a series of Z-folds, or a wall element comprising, or forming, a concertina. The bellow-based container or bioreactor may include a base section, a top section arranged substantially in parallel with the base section and a wall element arranged between the top section and the base section and defining an internal lumen of the container or bioreactor. The wall element of the container or bioreactor preferably is compressible with respect to the top and base sections. The wall element of the container or bioreactor may be composed of a flexible material. The wall element may comprise a series of Z-folds, that is, the wall element may comprise, or form, a bellows. The container may take the form of a concertina.

The term "auxiliary container" or "secondary container" is used to define that a container is connected to a second side, or surface, of the cell processing platform. For example, the term "auxiliary container" or "secondary container" may be used to define that the container is attached to an upper side, or surface, of the cell processing platform. There may be any number of auxiliary containers.

The auxiliary container may be a bellow-based container, for example, a bellow-based bioreactor. That is, the container or bioreactor may be based on a bellows, i.e., a container or bioreactor including a wall element comprising a series of Z-folds, or a wall element comprising, or forming, a concertina. The bellow-based container or bioreactor may include a base section, a top section arranged substantially in parallel with the base section and a wall element arranged between the top section and the base section and defining an internal lumen of the container or bioreactor. The wall element of the container or bioreactor preferably is compressible with respect to the top and base sections. The wall element of the container or bioreactor may be composed of a flexible material. The wall element may comprise a series of Z-folds. The wall element may comprise, or form, a bellows. The container may take the form of a concertina.

Generally, the term "container," or a "cell processing container," is used to define a container, a receptacle, a volume, a bioreactor, or the like in which one or more unit operations of cell and/or gene therapy manufacture or processing may be completed.

In certain embodiments, the body portion includes one, that is, a single, fluid inlet, and one, that is, a single, fluid outlet. In certain embodiments, the body portion includes one or more fluid inlets, and one or more fluid outlets. In certain embodiments, the body portion includes one, that is, a single, fluid inlet, and a plurality of fluid outlets. In certain embodiments, the body portion includes a plurality of fluid inlets, and one, that is, a single, fluid outlet. In certain embodiments, the body portions include a plurality of fluid inlets, and a plurality of fluid outlets.

In certain embodiments, the at least one auxiliary container is detachably connected to the auxiliary container port.

In certain embodiments, the primary container is detachably connected to the primary container port.

In certain embodiments, one or more auxiliary containers are indirectly fluidly coupled to the auxiliary container port. More specifically, one or more auxiliary containers may be connected to one another in series. Thus, an auxiliary container may be in fluid communication with a further auxiliary container, wherein the further auxiliary container is not in direct fluid communication with the auxiliary container port of the cell processing platform. Additionally, or alternatively, the cell processing device may further comprise one or more further containers, such as a bioreactor, in direct fluid communication with the primary container but not necessarily with the cell processing platform. In this way, the cell processing device may provide a multistage bioreactor operable to perform one or more unit processes in a cell and/or gene therapy manufacturing process.

In certain embodiments, the auxiliary container port comprises a container-receiving sleeve connected to the body portion and being configured to surround at least a portion of the auxiliary container, which portion comprises the fluid outlet of the container.

In certain embodiments, the container-receiving sleeve comprises insulation means configured to maintain the contents of an auxiliary container received in the sleeve at a particular temperature. More specifically, the insulation means is a thermal sleeve. Accordingly, an auxiliary container port may be configured to maintain the contents of an auxiliary container at an optimal temperature. For example, the optimal temperature may be a cell culture temperature (37 degrees Celsius), or room temperature (22 degrees Celsius), or refrigerated (e.g., around 4 degrees Celsius), or below freezing (e.g., around minus 4 degrees Celsius or lower, such as minus 20 degrees Celsius, or minus 80 degrees).

In certain embodiments, the cell processing device comprises one or more auxiliary container ports configured to maintain a variety of temperatures.

In certain embodiments, the cell processing platform comprises a plurality of auxiliary container ports and wherein each one of a plurality of auxiliary containers are received in sealing engagement with one of the plurality of auxiliary container ports such that the lumen of each auxiliary container is fluidly coupled with a fluid inlet of the body portion.

In certain embodiments, the auxiliary containers are detachably mounted to the auxiliary container ports.

In certain embodiments, each auxiliary container port is coupled to a separate fluid inlet of the body portion.

In certain embodiments, each separate fluid inlet of the body portion is fluidly connected to a fluid outlet of the body portion.

In certain embodiments, the at least one fluid inlet and the fluid outlet of the body portion are fluidly coupled to one another by a fluid conduit.

In certain embodiments, the fluid conduit comprises a valve operable to open and close the fluid conduit.

In certain embodiments, the valve is one of: a pinch valve, a pressure sensitive valve, a clamp valve, a membrane valve, a rupture disc, a venous valve and an aperture valve.

In certain embodiments, each auxiliary container port comprises a container filling port.

In certain embodiments, the container filling port is fluidly connected to a fluid inlet of the auxiliary container port.

In certain embodiments, each container filling port comprises a valve operatively coupled to the fluid inlet and a fluid outlet of the auxiliary container port and operable to control fluid flow direction through the auxiliary container port.

In certain embodiments, the container filling port comprises a valve operable, in an open position, to allow fluid to flow to the fluid inlet of the auxiliary container port and not to the fluid outlet of the auxiliary container port and, in a closed position, to close the container filling port and to allow fluid to flow from the fluid inlet of the auxiliary container port to the fluid outlet of the auxiliary container port.

In certain embodiments, the at least one auxiliary container comprises a mating element configured to fluidly connect to a corresponding mating element on the auxiliary container port.

In certain embodiments, the mating element is one of: a sterile connector end or a LUER-LOK™.

In certain embodiments, the primary container port comprises a mating element configured to fluidly connect to a corresponding mating element on the primary container.

In certain embodiments, the mating element comprises one of: a sterile connector end or a LUER-LOK™.

In certain embodiments, the auxiliary container port comprises a LUER-LOK™ connector at the fluid inlet and/or the fluid outlet of the auxiliary container port, each LUER-LOK™ connector configured to engage with a further LUER-LOK™ connector on a container and/or on the body portion, respectively. More specifically, a male LUER-LOK™ connector is configured to engage with a female LUER-LOK™ connector.

In certain embodiments, the fluid outlet of the body portion comprises a LUER-LOK™ connector configured to engage with a further LUER-LOK™ connector on a primary container attachable to the body portion.

In certain embodiments, the auxiliary container port comprises a sterile connector end at the fluid inlet and/or the fluid outlet of the auxiliary container port, each sterile connector end configured to engage with a further sterile connector end on a container and/or on the body portion, respectively.

In certain embodiments, the fluid outlet of the body portion comprises a sterile connector end configured to engage with a further sterile connector end on the primary container attachable to the body portion.

In certain embodiments, the cell processing device comprises at least one positional tracking device operable to indicate a set location on the cell processing platform. In this way, the position of the platform may be tracked, for example, when the cell processing device is mounted into a cell processing unit according to the disclosure.

In certain embodiments, the at least one positional tracking device is a mechanical device.

In certain embodiments, the at least one positional tracking device comprises a cog. In such embodiments, the mounting plate of the cell processing unit may comprise a further cog operable to engage the projections of the cog on the cell processing platform. In this way, the cell processing device will need to be physically inserted into the mounting plate of the cell processing unit in the correct orientation. This, in turn, ensures the operator knows the position of the device and thus containers mounted to the platform in the cell processing unit.

In certain embodiments, the positional tracking device is an encoder. More specifically, the positional tracking device is one or more of: a magnet, an RFID sensor, a light sensor or the like.

In certain embodiments, the cell processing device comprises a plurality of positional tracking devices.

In certain embodiments, the at least one positional tracking device is located on the cell processing platform relative to the auxiliary container port such that the location of the positional tracking device is related to the position of the auxiliary container port.

In certain embodiments, the at least one positional tracking device is located on the body portion of the cell processing platform relative to the auxiliary container port.

In certain embodiments, the system comprises a plurality of positional tracking devices each located on the body portion of the cell processing platform relative to an auxiliary container port.

In certain embodiments, the cell processing device comprises a sampling port in the body portion of the cell processing platform. Alternatively, the sampling port may be located in the base section of the primary container.

In certain embodiments, the cell processing device comprises a gas transfer port in the body portion of the cell processing platform. Alternatively, the gas transfer port may be located in the wall of the primary container.

In certain embodiments, the auxiliary container port is configured to receive a container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

In certain embodiments, the primary container port is configured to receive a primary container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

In certain embodiments, the primary container further comprises an attachment flange mounted to the top section of the primary container and being configured to sealingly engage and detachably mount to the primary container port.

In certain embodiments, the at least one auxiliary container is compressible. In this way, the container configuration is based on a concertina (which can act as a pump) therefore there is no need for separate pumps and complex sets of tubing/pipes to transfer the contents of a container to another container in the system. In turn this configuration reduces the space needed for a cell and/or gene therapy manufacturing process.

In certain embodiments, the container is a container described in patent application PCT/GB2016/051451.

In certain embodiments, the container is a container described in patent application PCT/GB2017/053389.

Alternatively, the container may comprise a syringe arrangement allowing it to be re-filled or emptied.

In certain embodiments, the at least one auxiliary container is a syringe. In such a syringe arrangement, the container has an arrangement analogous to a syringe having an element that is moveable to either expel fluid from the container or draw it back in.

In certain embodiments, the container may comprise any shaped container with a moving seal allowing variable volume operations.

In certain embodiments, the at least one auxiliary container is a bag retained in a frame and moveable with respect to the frame. More specifically, the top section, the base section and wall element of the at least one auxiliary container may form a bag that can be held within an external adjustable frame, or in which the bag comprises an internal adjustable frame within the material of the bag. Accordingly, one or more of the auxiliary containers in fluid communication with a cell processing platform of the disclosure may form a bag that can be held within an external adjustable frame, or in which the bag comprises an internal adjustable frame within the material of the bag. Such a bag may be configured to act, for example, as an intravenous drip bag. It will therefore be understood the product(s) of any reaction(s) carried out in a primary container or further container of the cell processing device may be collected into the bag, which can then be removed and transferred to an intravenous drip. Alternatively, the product(s) of any reaction(s) can be directly delivered to a patient from the lumen of the container.

In certain embodiments, the cell processing device comprises one or more auxiliary containers connected to an auxiliary container port of the cell processing platform. More specifically, the one or more auxiliary containers are detachably connected to an auxiliary container port of the cell processing platform.

In certain embodiments, one or more of the auxiliary containers are connected to a respective auxiliary container port with a sterile connector.

In certain embodiments, one or more of the auxiliary containers are connected to a respective auxiliary container port with a LUER-LOK™ style connector.

In certain embodiments, the at least one auxiliary container is located on the top of the cell processing platform.

In certain embodiments, the primary container is located on the bottom of the cell processing platform.

According to a further aspect, the present disclosure provides a multi-step method of performing one or more unit operations in cell and/or gene therapy manufacture using a cell processing device according to the disclosure.

In certain embodiments, the method comprises introducing a cell population, for example, a cell population of interest, into the primary container and sequentially adding one or more reagents from one or more auxiliary containers into the primary container via the cell processing platform in order to effect growth, culturing and/or modification of the cells, for example, in order to effect a desired growth, culturing and/or modification of the cells.

In certain embodiments, the auxiliary container is one of: a reagent container, a cell culture container, a waste container, an empty container or a bioreactor.

In certain embodiments, the primary container is one of: a cell culture container or a bioreactor, a reagent container, a waste container, a filter, an electroporator, a purifier, a waste container, a filter, an electroporator, a purifier, holding container, apheresis/leukopheresis, differentiation chamber, chromatography column, settling chamber, sieve, shaking/mixer, a centrifuge and a magnetic bead separator or the like.

A container of the disclosure may be of circular, square, rectangular, elliptical, or triangular cross section. Alternatively, a container of the disclosure may comprise a number of different sections or regions of a variety of cross sections, such as, for example, a series of circular cross sections with variable (increasing and/or decreasing) diameters.

Advanced blow molding techniques can be used to deposit a second (or even third), external, coating or layer of plastic impermeable to oxygen onto the wall, top and base of the auxiliary container. In this way, shelf life of the container in storage can be extended.

According to a yet further aspect the present disclosure provides a cell processing system comprising a cell processing device according to an aspect of the disclosure and a cell processing unit according to the disclosure.

Cell Processing Container

A critical step, and risk, in performing unit operations in cell and/or gene therapy manufacture, is the sterile connection of the components of the equipment to form a usable cell processing device or the like.

At least this object and advantages that will be apparent from the description have been achieved by a cell processing container for use in one or more unit operations in cell and/or gene therapy manufacture, the container having a base section, a top section arranged substantially in parallel with the base section and a wall element arranged between the top section and the base section and defining an internal lumen of the container, in which the wall element of the cell culture container preferably is compressible with respect to the top and base section and the wall element of the cell culture container is composed of a flexible material, wherein the cell processing container comprises at least one sterile connector end configured to operatively couple with a further sterile connector end to form a sterile connector between the cell processing container and a further component to which the cell processing container is to be fluidly connected.

A sterile connector when referred to herein shall at least include a sterile connecting device configured to produce a sterile connection or sterile welds between two elements, for example, two containers or two pieces of compatible tubing. This procedure permits sterile connection of a variety of containers and tubes of varying diameters by maintaining a closed system as the two portions of the sterile connecting device are mated with one another. In this way, a sterile fluid pathway is maintained between two elements, for example, containers, tubes or the like. Each tube/container may have a sterile connector end embedded therein and may have a removable membrane (e.g., paper) or valve barrier for mating to another connector end embedded in a further tube/container. Sterile connectors are designed to connect one processing stream to another, such as a container to a sampling line, media to a product vessel, or a filtration assembly to a filling line. They become beneficial when no biocontainment hood is available to make an aseptic connection as, owing to the aseptic pathway created, a sterile connection can be achieved irrespective of the environment or surroundings in which the connection is made.

The line at the junction of the connection cannot be disconnected without force because of safety mechanisms in place to prevent this. Disconnection between connected sterile connector ends may, for example, require a disconnection device, tube sealer, or tube crimper.

The term "fluidly connected" is used to refer to a connection between components to allow passageway of a fluid. The term "fluid" is used to refer to gases and liquids, in addition to solutions, suspensions, pastes and gels. Moreover, fluid may also refer to granular particulates, or solids, such as powders. Such particulates, solids or powders may or may not be suspended within a liquid, as a solution, or the like.

In some examples, the wall element of the cell processing container preferably, that is, optionally, is compressible with respect to the top and base section. That is, the top section may be compressed with respect to the base section, or the base section may be compressed with respect to the top section, or the top section and the base section may be compressed with respect to the base section and the top section, respectively.

In other examples, the wall element of the cell processing container is not compressible with respect to the top and base sections. In some examples, the wall element of the cell processing container may be flexible, such that a compression, or squeezing, of the wall element inwardly toward a central longitudinal axis may be achieved.

Generally, the term "container," or "cell processing container," is used to define a container, a receptacle, a volume, a bioreactor, or the like in which one or more unit operations of cell and/or gene therapy manufacture or processing may be completed.

In certain embodiments, the at least one sterile connector end is a genderless sterile connector end configured to operatively couple with a further genderless sterile connector end.

That is, the at least one sterile connector end may be genderless in the sense that it includes neither a male portion nor a female portion. In some examples, the genderless sterile connector end may include one or more portions that cooperate with a portion of a further genderless sterile connector end.

In certain embodiments, the at least one sterile connector end is a male sterile connector end configured to operatively couple with a female sterile connector end.

In certain embodiments, the at least one sterile connector end is a female sterile connector end configured to operatively couple with a male sterile connector end.

In certain embodiments, the cell processing container comprises a plurality of sterile connector ends each configured to operatively couple with a separate further sterile connector end to form a plurality of sterile connectors between the cell processing container and at least one further component to which the cell processing container is to be fluidly connected.

In certain embodiments, the at least one further component is one of: a further cell processing container, a cell processing platform according to the disclosure, a tube or the like.

In certain embodiments, the sterile connector ends are embedded in the cell processing container.

In some examples, the sterile connector ends may form part of the cell processing container. In some examples, the sterile connector ends may form an integral part, or may be integrally formed within, or as part of, the cell processing container.

In certain embodiments, the sterile connector end is operatively coupled to a pinch valve embedded in the cell processing container.

In certain embodiments, the cell processing container has a circular, square, rectangular, elliptical, or triangular cross section.

In certain embodiments, when the cell processing container has a circular shape, the sterile connector end(s) is/are connected to the top and/or base section of the cell processing container in an essentially circular pattern.

According to an aspect of the disclosure there is provided a cell processing system, comprising a cell processing container as described above, further comprising one or more auxiliary containers detachably connected to the cell processing container.

In certain embodiments, one or more of the auxiliary containers comprises the further sterile connector end and is connected to the cell processing container via the further sterile connector end.

In certain embodiments, one or more of the auxiliary containers is located at or near the top section of the cell processing container.

In certain embodiments, one or more of the auxiliary containers is located on the top section of the cell processing container.

In certain embodiments, one or more of the auxiliary containers is located on the top section of the cell culture container.

In certain embodiments, one or more of the auxiliary containers is located at or near the base section of the cell processing container.

In certain embodiments, one or more auxiliary containers are located on the top section of the cell processing container.

In certain embodiments, one or more of the auxiliary containers is located on the base section of the cell culture container.

In certain embodiments, one or more containers may be connected in series. For example, the cell processing system of the disclosure may comprise an auxiliary container that is in fluid communication with a further auxiliary container, wherein the further auxiliary container is not is direct fluid communication with the cell processing container of the system.

In certain embodiments, each container in a series of containers comprises a sterile connector end in a top and in a base section. In this way, it is possible to undertake one or more processing steps in an auxiliary container before making a sterile connection via the sterile connector ends in connected containers in order to undertake one or more further processing steps in the combined containers. In certain embodiments, the one or more processing steps and the one or more further processing steps may involve different cell processing units.

In certain embodiments, the one or more auxiliary containers have a base section, a top section arranged substantially in parallel with the base section and a wall element arranged between the top section and the base section and defining an internal lumen of the container, in which the wall element of the auxiliary container preferably is compressible with respect to the top and base section and the wall element of the auxiliary container is composed of a flexible material.

Advanced blow molding techniques can be used to deposit a second (or even third), external, coating or layer of plastic impermeable to oxygen onto the wall, top and base of the auxiliary container. In this way, shelf life of the container in storage can be extended.

According to a yet further aspect of the disclosure there is provided a cell processing system operable to perform one or more unit operations in cell and/or gene therapy manufacture. The cell processing system comprises, a cell processing unit according to an aspect of the disclosure, a cell processing device according to an aspect of the disclosure comprising a cell processing platform according to an aspect of the disclosure.

In certain embodiments, the cell processing system comprises at least one cell processing container according to an aspect of the disclosure.

According to a yet further aspect of the disclosure there is provided a multi-step method of one or more unit operations in cell and/or gene therapy manufacture using a cell culture system according to the disclosure.

In certain embodiments, the method comprises introducing a cell population, for example, a cell population of interest, into the cell processing container and sequentially adding one or more reagents from one or more auxiliary containers into the cell processing container in order to effect one or more unit operations in cell and/or gene therapy manufacture, for example, desired one or more unit operations in cell and/or gene therapy manufacture.

As will be clear to the person skilled in the art, elements, components, features and advantages of the cell processing unit, cell processing platform, cell processing device, cell processing container, sterile connector ends, and the methods of manufacture, usage and components thereof may be applied equally to various embodiments described herein. That is, where a feature is described in relation to one embodiment, aspect or example, this is not intended to preclude the inclusion of such a feature in relation to another embodiment, aspect or example, as will be recognized by those skilled in the art.

BRIEF DESCRIPTION OF THE DRAWINGS

These and other aspects, features and advantages of which embodiments of the disclosure are capable of, will be apparent and elucidated from the following description of embodiments and aspects of the present disclosure, reference being made to the accompanying drawings, in which.

DETAILED DESCRIPTION

Figure 1:
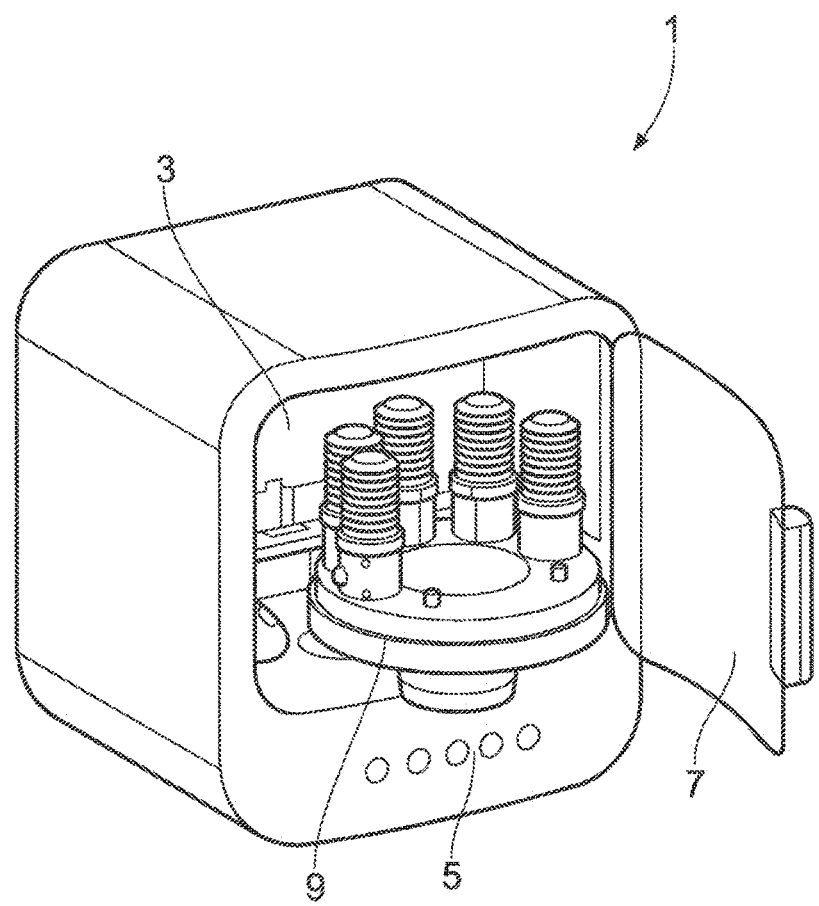
FIG. 1 illustrates a perspective view of a cell processing unit according to an embodiment of the disclosure with a cell processing device partially loaded into the device.

Specific embodiments of the disclosure will now be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. The terminology used in the detailed description of the embodiments illustrated in the accompanying drawings is not intended to be limiting of the disclosure. In the drawings, like numbers refer to like elements.

The terminology used herein is for the purpose of describing particular aspects of the disclosure only, and is not intended to limit the disclosure. As used herein, the singular forms "a," "an" and "the" are intended to include the plural forms as well, unless the context clearly indicates otherwise.

In the drawings and specification, there have been disclosed exemplary aspects of the disclosure. However, many variations and modifications can be made to these aspects without substantially departing from the principles of the present disclosure. Thus, the disclosure should be regarded as illustrative rather than restrictive, and not as being limited to the particular aspects discussed above. Accordingly, although specific terms are employed, they are used in a generic and descriptive sense only and not for purposes of limitation, for example, definition of dimensions such as width or breadth or height or length or diameter depends on how exemplary aspects are depicted, hence, if depicted differently, a shown width or diameter in one depiction is a length or thickness in another depiction.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example aspects may be implemented at least in part by means of both hardware and software, and that several "means," "units" or "devices" may be represented by the same item of hardware.

Features, integers, characteristics, compounds, chemical moieties or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

In the drawings like reference numerals refer to like parts.

Cell Processing Unit

FIG. 1 illustrates a cell processing unit 1 according to the present disclosure. The cell processing unit comprises a housing 2 formed of four walls upstanding from a base wall and a top wall parallel to the base wall and spaced apart from it by the length of the walls. The housing 2 forms a chamber 3 with a hinged door 7 in one wall for receiving a cell processing device 901 comprising cell processing platform (CPP) 9. On the front panel of the cell processing unit 1 is a control panel 5 to enable the user to program and control various features positioned within the chamber 3, as well as their interactions with the cell processing device 901. Details of these features and the cell processing device 901 are set out in more detail below.

The cell processing unit 1 has a housing 2 that defines an enclosed space, being chamber 3, in which one or more unit operations (i.e., steps) of cell and/or gene therapy manufacturing process can occur.

Figure 2:
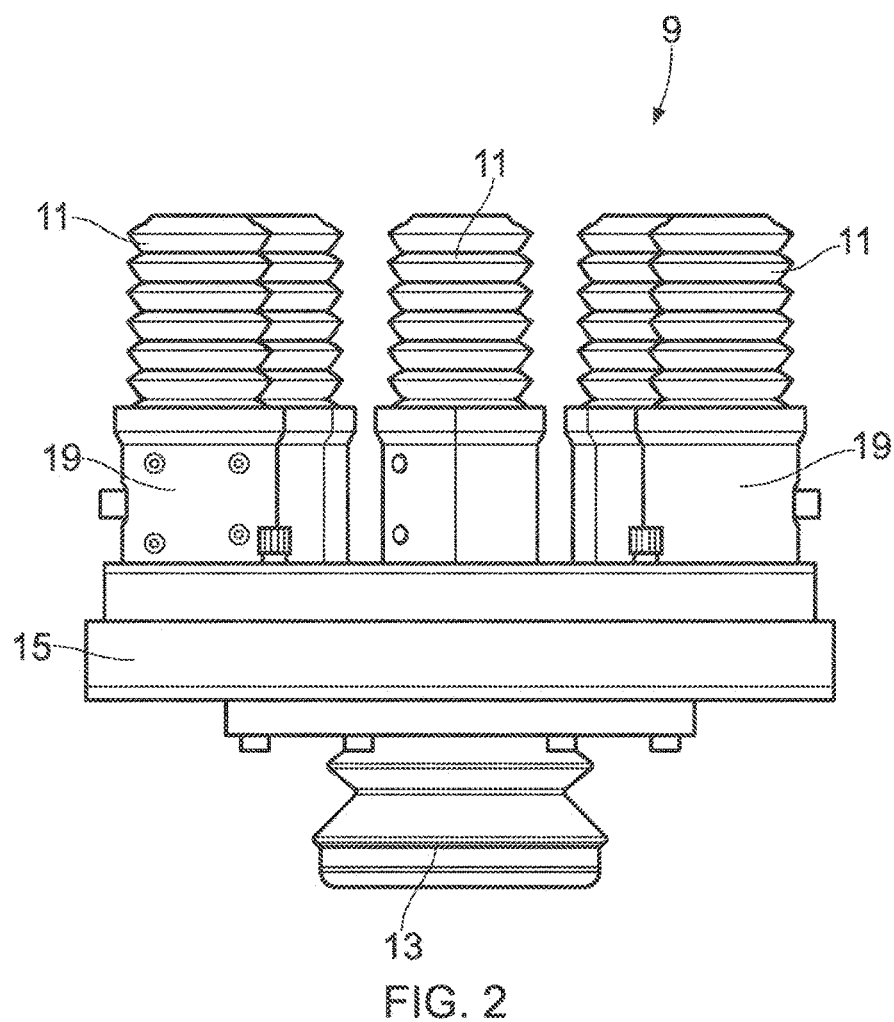
FIG. 2 illustrates a side view of a cell processing device according to an embodiment of the disclosure.

An automated cell processing system according to an embodiment of the disclosure comprises cell processing unit 1 and a cell processing device 901 as shown in FIG. 2. The cell processing device 901 comprises a cell processing platform 9 and one or more auxiliary containers 11 coupled to the cell processing platform 9. The cell processing platform 9 can be manipulated by the cell processing unit 1 to transfer liquids between the auxiliary container 11 (e.g., feed bellows) located on the top of the cell processing platform 9 and the primary container 13 (e.g., reactor bellow) located on the bottom of the cell processing platform 9. FIG. 1 shows an embodiment in which the cell processing system has cell processing unit 1 and a cell processing device 901 with five auxiliary containers 11 fluidly connected to the cell processing platform 9. The cell processing unit 1 rotates the cell processing platform 9 using a friction drive system. The cell processing unit 1 comprises a valve solenoid microlinear actuator (38, FIG. 6A) that, when activated, opens valve means 27 in the cell processing platform 9 and presses the auxiliary container 11 using a linear actuator (106, FIG. 6A). The cell processing platform 9 comprises a body portion comprising base plate 15 onto which the primary container 13 (e.g., reactor bellow) is fitted on the underneath into a primary container port (FIG. 2, reference numeral 14) and the five auxiliary containers 11 (e.g., feed bellows) are fitted on top of the base plate 15 in auxiliary container ports 19. The auxiliary containers 11 (e.g., feed bellows) are mounted on top of the sleeves forming the auxiliary container ports 19 that contain LUER-LOK™ fittings to connect the auxiliary containers 11 to the tubing in the auxiliary container ports 19. The tubing is fluidly connected to the tubing in the base plate 15, through the base plate 15, and onto the fluid outlet at the primary container port 14. Each auxiliary container port 19 comprises a filling port 31 that allows for filling of the auxiliary container 11 fluidly coupled to the auxiliary container port 19. The base plate 15 of the cell processing platform 9 contains normally closed valve means 27 acting on the tubing 29 between the auxiliary containers 11 and the primary container 13. In this embodiment, the cell processing system comprises a cell processing device with five auxiliary containers. However, it should be appreciated that in cell processing device may have a different number of auxiliary containers according to the present disclosure. It is further envisaged that the containers may have different volumes according to the present disclosure.

The chamber 3 is not sterile; however, the containers are completely closed when loaded into the cell processing platform. The containers in parallel and/or series in the cell processing platform provide a single closed consumable unit (cell processing device) for the entire manufacturing process. Filling the containers occurs either aseptically (e.g., in a laminar flow hood) or using sterile connections (e.g., tube welding or sterile connections).

The housing 2 of the cell processing unit 1 allows for easy insertion and removal of the cell processing device 901 through a front opening door 7. With the door 7 open, the cell processing device 901 comprising the cell processing platform 9 and attached auxiliary containers 11 each comprising various cell processing reagents can be placed down and slid into its final position. The control panel 5 is located on the front of the housing 2, meaning that all interactions with the cell processing unit 1 happen from the front. In this way, multiple cell processing units 1 can be placed close together, side by side or on top of each other. Having rows of units or stacks of units, respectively, facilitates the capacity for advanced manufacturing and processing. The depicted embodiment is shown with five buttons, one for each feed actuation in a test protocol for the system. The door 7 is transparent so that the operations can be visible when demonstrating the function of the apparatus. In alternative embodiments, an opaque door could be provided. In this way, the cells can be shielded from UV light during processing.

Cell Processing Unit

Figure 6A:
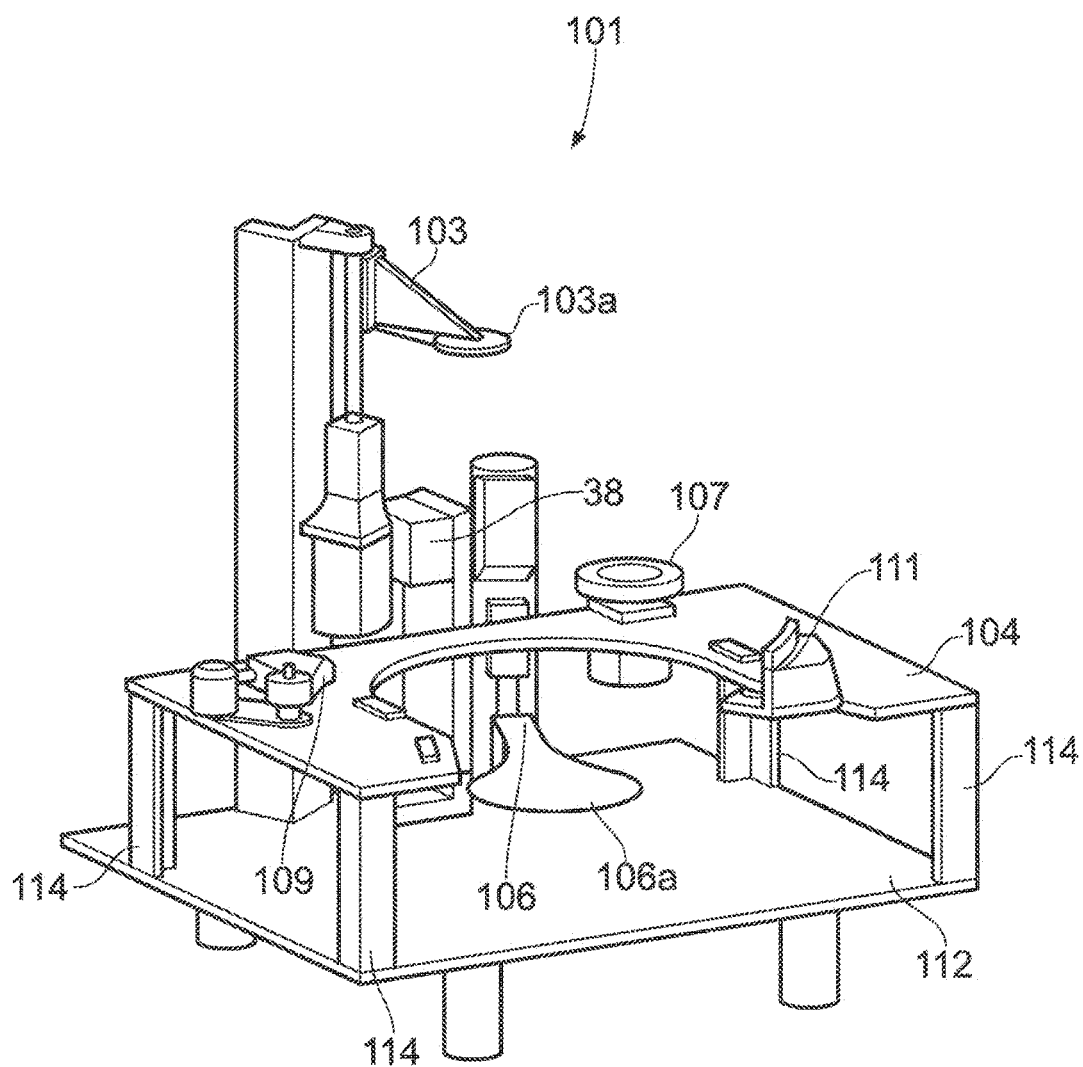
FIG. 6A illustrates a perspective view of the mounting bracket, actuators and frictional drive mechanism of the cell processing unit of FIG. 1.
Figure 6B:
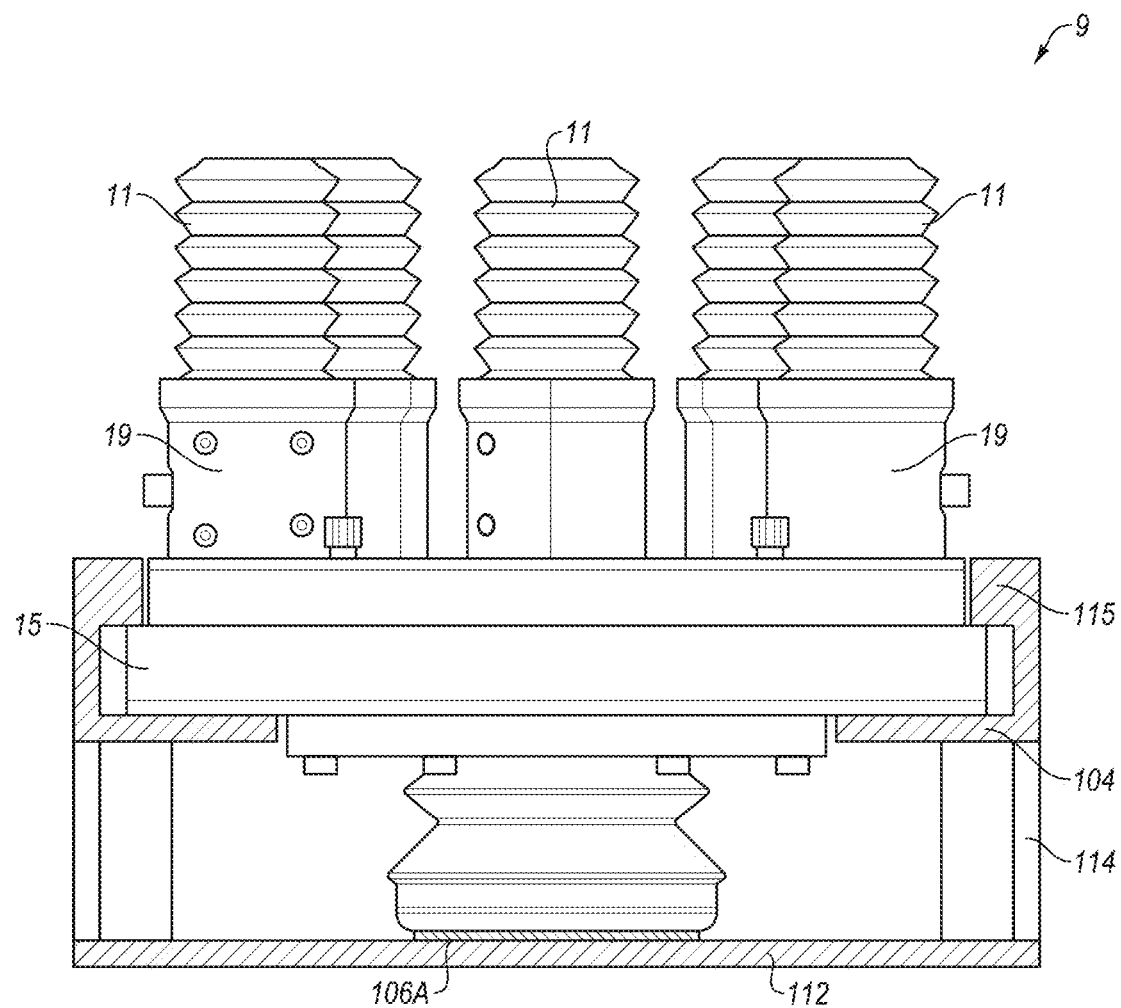
FIG. 6B illustrates a side view of the mounting bracket of FIG. 6A and the cell processing device of FIG. 2.

FIG. 6A shows a portion 101 of cell processing unit 1 with the housing 2 removed for ease of depiction. FIG. 6B illustrates a side view of the mounting bracket of FIG. 6A and the cell processing device 9 of FIG. 2. Inside the housing, the portion 101 of the cell processing unit comprises a linear actuator 103 for compression of the auxiliary container 11 feed bellows, a linear actuator 106 for compression of the primary container 13 reactor bellow, a friction drive mechanism (107, 109, 111) mounted on mounting plate 104 and operable to rotate the cell processing platform 9 and a micro linear actuator 38 for opening the pinch valves that are operable to open and close the tubing in the platform. The internal structure of the apparatus is machined from aluminum, the linear actuators 106, 103 are aluminum and steel constructions with the lead screws hard coated in TFE dry lubricant.

In addition to the mounting plate 104, the mounting bracket comprises a mounting flange 115, located above the mounting plate in such a way as to retain the cell processing platform by frictional fit between the mounting plate 104 and the mounting flange 115.

The layout of the actuators 38, 103, 106 allows them to be hidden in the rear of the apparatus by a cover (not shown) through which only the plungers 103a, 106a protrude to compress the bellows of the auxiliary and primary containers, respectively, helping to give a clean and uncomplicated appearance, and provides an apparatus that is simpler to clean and wipe down. A power supply and the electronics for the actuators and the frictional drive mechanism are mounted on the plate 112 below the mounting plate 104. The four risers 114 are adjustable in height and operable to change the distance between the mounting plate 104 and the plate 112 housing the power supply and the electronics. In this way, the apparatus can accommodation different sizes of primary containers.

The housing 2 contains all of the actuators and electronics necessary to manipulate the cell processing device. The feed bellow plunger 103a and reactor plunger 106a operable to exert a compression force on the auxiliary container and the primary container, respectively, attach to linear rails, each with a maximum force of 100 N. The motors driving the linear rails are bipolar stepper motors. The valve actuator 38 is a linear actuator with a maximum force of 45N.

The frictional drive mechanism (107, 109, 111) comprises a drive wheel 107 located on mounting plate 104 and operable to impart rotation on the cell processing device. The drive wheel 107 is a bipolar stepper motor. The actuator stepper motors on the linear rails and the stepper motor in the frictional drive mechanism are driven by a control system and associated power supply (not shown).

Figure 7:
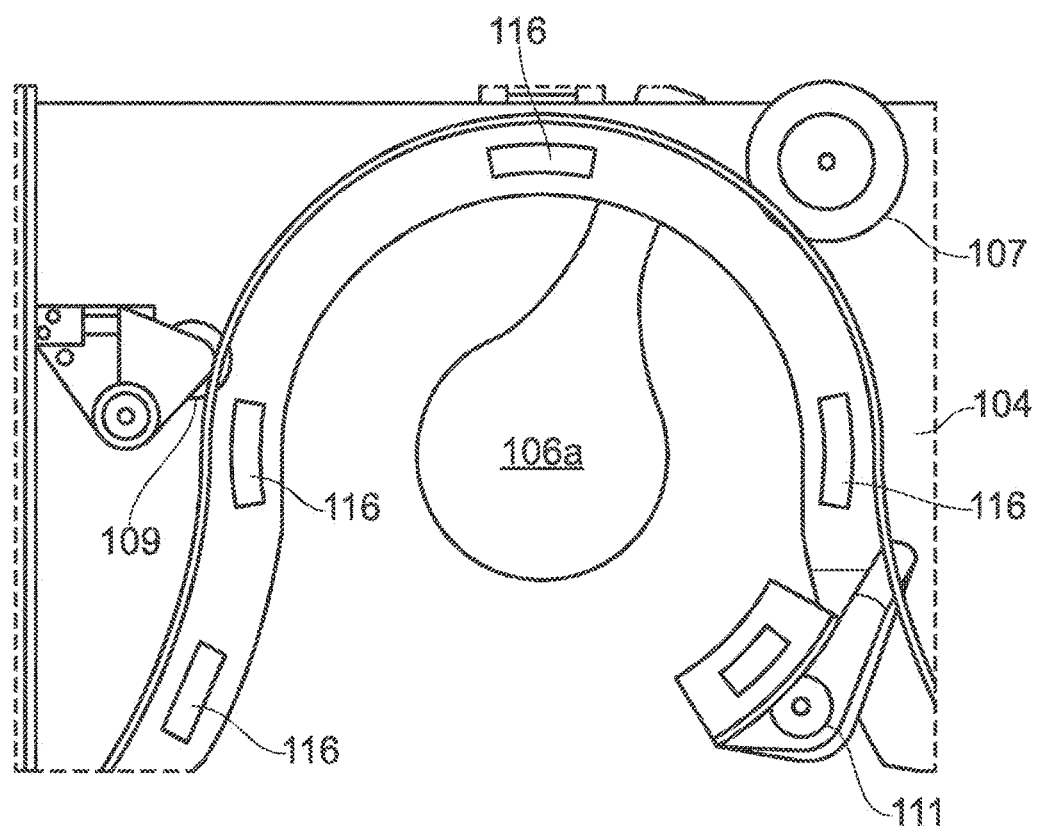
FIG. 7 illustrates a top view of the mounting plate and the frictional drive mechanism of the partial cell processing unit of FIG. 6A.

FIG. 7 shows the elements of the frictional drive mechanism (107, 109, 111) mounted to the mounting plate 104 of the mounting bracket. To allow the cell processing device 901 comprising the cell processing platform 9 and the auxiliary containers to be inserted from front only, a drive method has been developed where the cell processing platform 9 is held between three friction wheels, one of which being a drive wheel 107, the other a spring-loaded friction wheel 109 and the third being a hinge wheel 111 within the door that opens to allow insertion of the cell processing platform 9 and closes to lock it in place. The cell processing device 901 rotates on low friction PTFE pads 116 on the mounting plate 104. The spring force of the sprung friction wheel 109 will be such that there is no slip between the drive wheel 107 and the outer face of the base plate 15 of the cell processing platform 9. The drive wheel 107 is directly connected to a stepper motor. The base plate 15 of the cell processing platform 9 is fitted with a series of magnets 118 around its circumference so that its position can be read by a Hall Effect sensor 120 mounted on the mounting plate 104. The cell processing platform 9 therefore acts like an encoder and gives closed loop position feedback independent of any motor slip.

Figure 8:
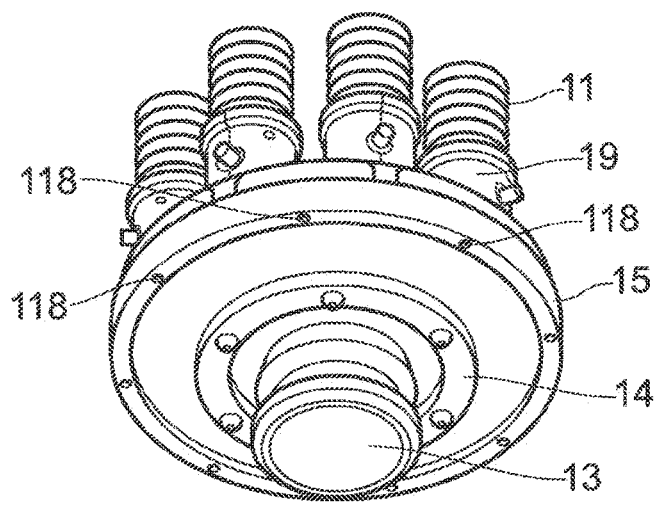
FIG. 8 illustrates a perspective view of the underside of the cell processing device of FIG. 2.
Figure 9:
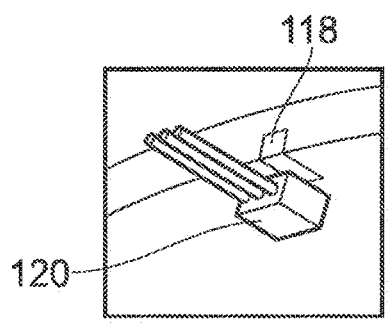
FIG. 9 illustrates a close up view of the cell processing device and sensor arrangement of FIG. 8.
Figure 10:
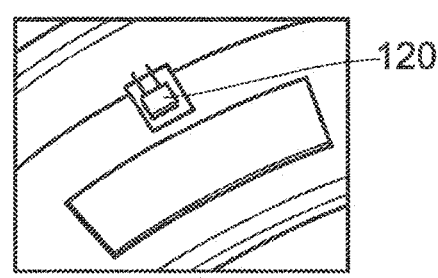
FIG. 10 illustrates a top view of the cell processing device and sensor arrangement of FIG. 8.
Figure 11:
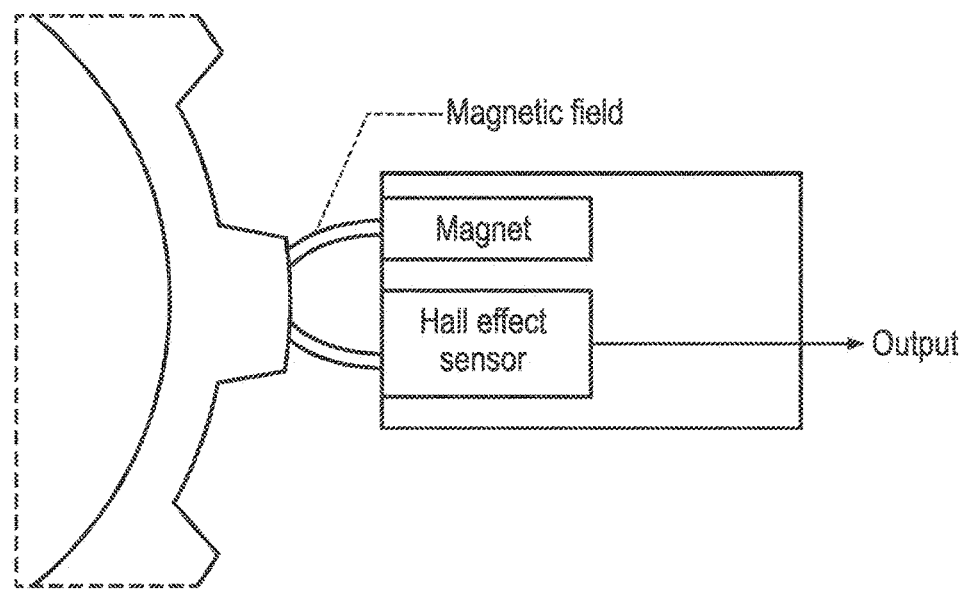
FIG. 11 illustrates a Hall Effect Sensor of the cell processing unit and a cell processing platform comprising at least one magnet.

The Hall Effect sensor 120 mounted to the mounting plate 104 attached to the housing 2 is operable to detect the magnetic field from the magnets 118 on a cell processing platform 9 mounted in the housing 2. The Hall Effect sensor 120 is operable to detect the position of the cell processing platform 9 relative to the mounting plate 104. As best seen in FIG. 8, each auxiliary container port 19 attached to the base plate 15 of the cell processing platform 9 has a magnet 118 positioned in the base plate 15 adjacent the auxiliary container port 19. In this way, the Hall Effect sensor 120 will detect a magnet 118 when an auxiliary container port 19 and its associated magnet 118 are in line with the sensor. Therefore the respective auxiliary container port 19 is in a known position in the housing relative to the mounting plate 104.

FIGS. 8, 9, 10 and 11 show the positional sensor array operable to detect the position of the cell processing platform 9 of the cell processing device within the cell processing unit 1.

The sensor array comprises Hall Effect sensors 120 and a series of magnets 118 on the base plate 15. The sensor array tracks the position of the cell processing platform 9 using the Hall Effect sensors 120. The Hall Effect sensors 120 produce a voltage in response to magnetic fields produced by magnets 118. There are two Hall Effect sensors 120 mounted to the mounting plate 104 in the housing 2 and a series of magnets 118 embedded in the cell processing platform 9. One of the Hall Effect sensors 120 is for tracking rotation of the cell processing platform 9 relative to the mounting plate 104 and the other Hall Effect sensor 120 is dedicated to tracking a so-called home position of the cell processing platform 9 relative to the mounting plate 104. The home position is determined by having one magnet 118 on a different pitch circle diameter to the other magnets 118 on the cell processing platform 9, serving as an index or marker to count full revolutions of the cell processing platform 9 in the housing 2. Using the cell processing device as an encoder, rather than having an encoder on the motor, means that there is a closed loop position feedback on the cell processing device itself.

To ensure there will be no slip between the drive mechanism and the cell processing platform 9, the friction between the elastomeric drive (friction) wheel 107 and the base plate 15 needs to be greater than the friction between the PTFE pads 116 and the base plate 15. Using the maximum force that will be transmitted between the drive wheel 107 and the base plate 15 of the cell processing platform 9, the normal force required to ensure consistent drive can be calculated.

Cell Processing Device

The cell processing platform 9, as shown in FIGS. 2-5, comprises a cell processing platform having an annular base plate 15 with a number of auxiliary container ports 19, in this case five, arranged on the upper surface, and a single primary or reactor container 13 mounted on its underside at a primary container port 14. Each auxiliary container port 19 is adapted to receive an auxiliary container 11, such as the types described herein, or in publication WO2018087558. Each of the auxiliary containers 11 in the example has a 45 ml maximum capacity such that the total feed capacity of the five auxiliary containers 11 is 225 ml. The primary container 13 has a maximum capacity of 150 ml.

Figure 3:
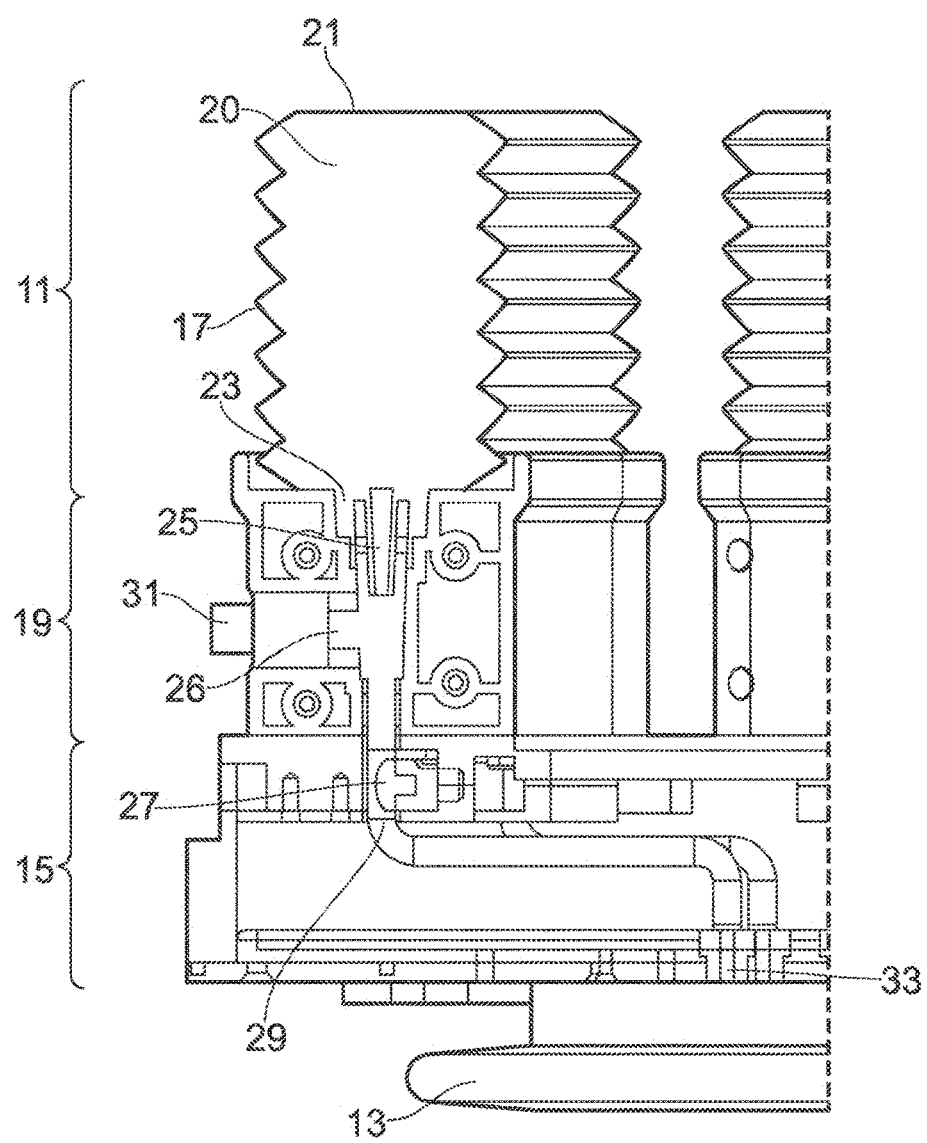
FIG. 3 illustrates a cross-sectional view of a part of the cell processing device of FIG. 2.

As shown in the cross-section of FIG. 3, the auxiliary container 11 comprises a top section 21 and a base section 23 with a collapsible bellows portion 17 located between them to define a storage volume 20. The base section 23 includes fluid outlet 25 through which the contents of the storage volume 20 can be transferred. With the auxiliary container 11 located into auxiliary container port 19, the fluid outlet 25 is in fluid communication with a connector 26 located therein. In the example shown, the connector 26 comprises a 4-way stopcock described in more detail below.

The auxiliary containers 11 are formed of blow molded LDPE while the auxiliary container ports 19 are formed of Nylon. The base plate 15 is formed of machined HDPE and the primary container 13 is formed of blow molded HDPE bonded to a machined HDPE flange being the primary container port 14. The base plate 15 is made up of three pieces that are screwed together. The primary container 13 is mounted to the base plate 15 by screws.

A flexible tubing 29 comprises a first end fitted to connector 26, and a second end fitted to base plate outlet 33, thereby forming a fluid communication conduit between the auxiliary container 11 and the primary container 13. The flexible tubing 29 may comprise any appropriate length and cross section. In the example show, the flexible tubing 29 is COLE-PARMER® Platinum Cured Silicone Tubing with inner diameter (ID) ⅛" and outer diameter (OD) 3/16". Aptly, the flexible tubing will be made from a suitably non-leachable, resilient and biologically inert material, in this case silicone, although other resilient materials may be used.

Fluid flow through the fluid communication conduit, and hence between an auxiliary container 11 and the primary container 13 is controlled by valve means 27, located within the base plate 15. In the example shown, the auxiliary container 11 is one of several, each located in a corresponding auxiliary container port 19 on the base plate 15. Accordingly, each auxiliary container 11 is provided with a unique fluid communication conduit (e.g., flexible tubing 29) to the primary container 13, controlled by a separate valve means 27. In this way, the transfer of the contents of each storage volume 20 may be precisely and independently controlled.

Figure 4A:
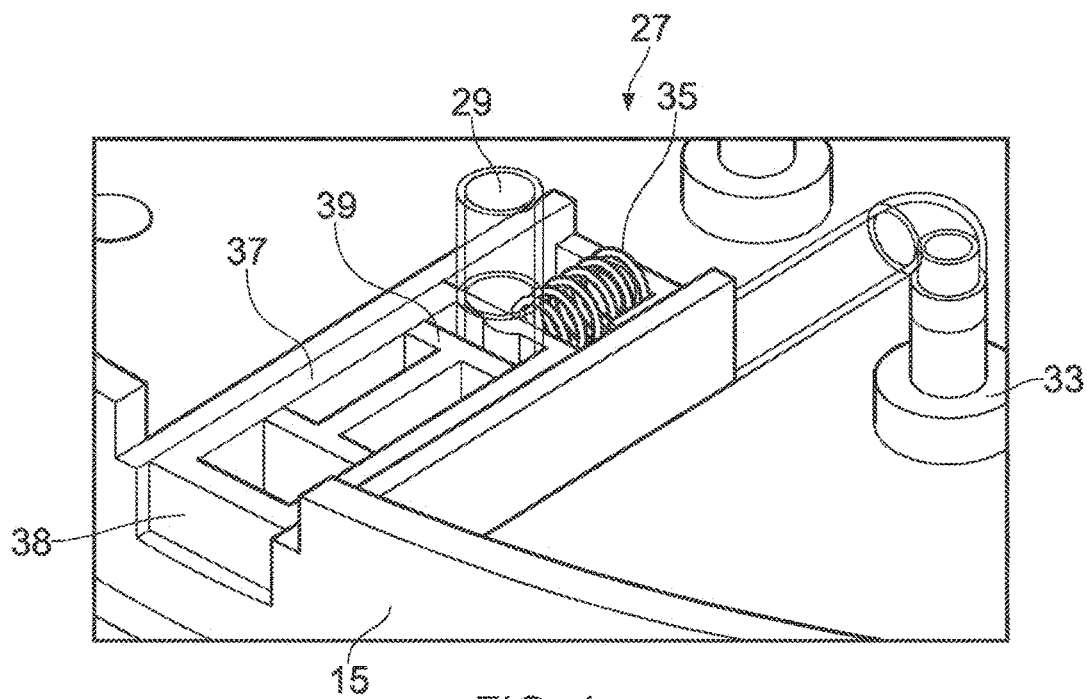
FIGS. 4A and 4B illustrate a perspective view of the valve means of the cell processing platform of the cell processing device of FIG. 2.
Figure 4B:
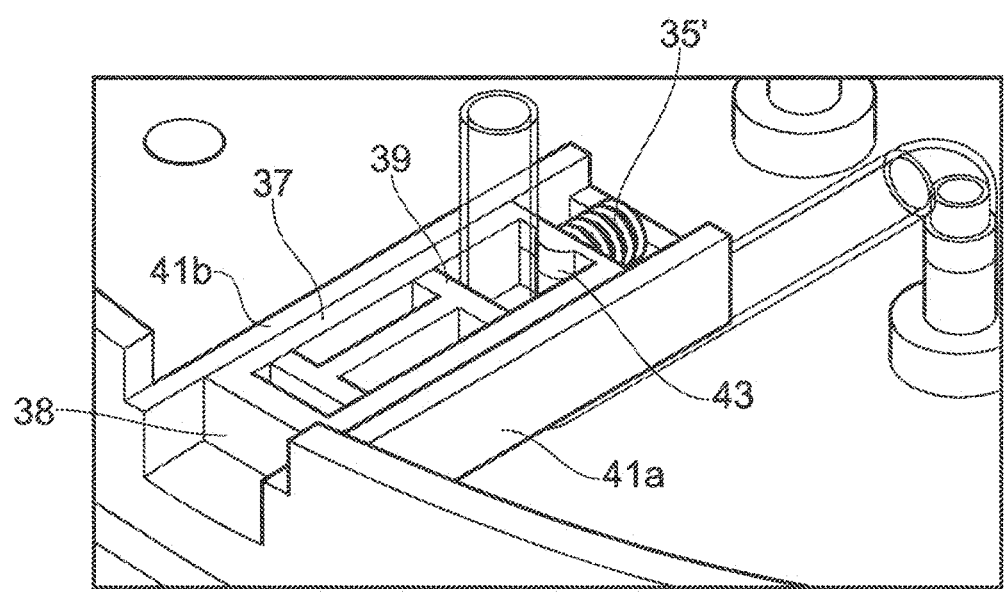

One of the valve means 27 is shown in more detail in FIGS. 4A and 4B. The valve means 27 comprises a closure portion 37 slidably engaged within a radial channel located in the base plate 15 and defined between channel walls 41a and 41b. The closure portion 37 is substantially a hollow rectangular shape with the longer pair of opposing walls arranged parallel with the channel walls 41a and 41b and the shorter pair of opposing walls arranged at its inner and outer surfaces. An actuating portion 38 is provided on the outer short wall and a compression portion 43 is provided on the inner shorter wall.

The closure portion 37 is located over a valve wall 39 fixed within the channel and spaced away from the channel walls 41a and 41b. The closure portion 37 can thus be moved between two extreme positions—a closed position (FIG. 4A) and an open position (FIG. 4B)—by sliding past the valve wall 39 within the channel.

The flexible tubing 29 is arranged to extend through the valve means 27 such that a section of the tubing 29 sits between the valve wall 39 and the compression portion 43. In the closed position, the closure portion 37 is urged toward the outer perimeter of the base plate 15 by a spring 35. The spring 35 is positioned to act on the compression portion 43, urging it against the flexible tubing 29 and pinching it against the valve wall 39. Thus, in the closed position, the pinched section of tubing blocks the fluid communication conduit and prevents fluid flow.

To unblock the conduit, the closure portion 37 is moved toward the open position by pressing the actuating portion 38, releasing the compression portion 43 from the valve wall 39 and allowing the pinched section of the flexible tubing to revert to its original shape and permitting fluid flow.

With the cell processing device installed in the cell processing unit, the valve means 27 is actuated by actuator 38 and opened while the auxiliary container 11 is compressed by plunger 103a. The actuator 38 may be configured so that the valve means 27 opens when the auxiliary container 11 is compressed. Alternatively, actuation may occur as a separate step, for example, when the auxiliary container 11 is received into the auxiliary container port 19. The actuation may occur automatically in conjunction with the compression of the auxiliary container 11, or may be controlled to happen independently.

In the example shown, the valve actuation is carried out by a linear actuator 38 located at the rear of the chamber 3 of the cell processing unit 1, which acts upon the closure portion 37 to move it toward the open position. Thus, the valve means is normally closed and actuated to open only when fluid needs to be delivered to the primary container 13.

As shown in FIG. 3, each auxiliary container 11 is attached to a filling valve connector 26 in the form of a 4-way stopcock. The connector 26 comprises a LUER-LOK™ port for filling via direct access to the auxiliary container 11. This port, which may be used for manually inserting fluids into the auxiliary container, does not have its own valve means 27, but is capped instead.

Two further capped LUER-LOK™ ports are provided on base plate 15 for sampling/harvesting fluid, or gas exchange. A first port leads to the head space of the primary container, while a further port is connected to the base of the primary container 13.

Figure 5:
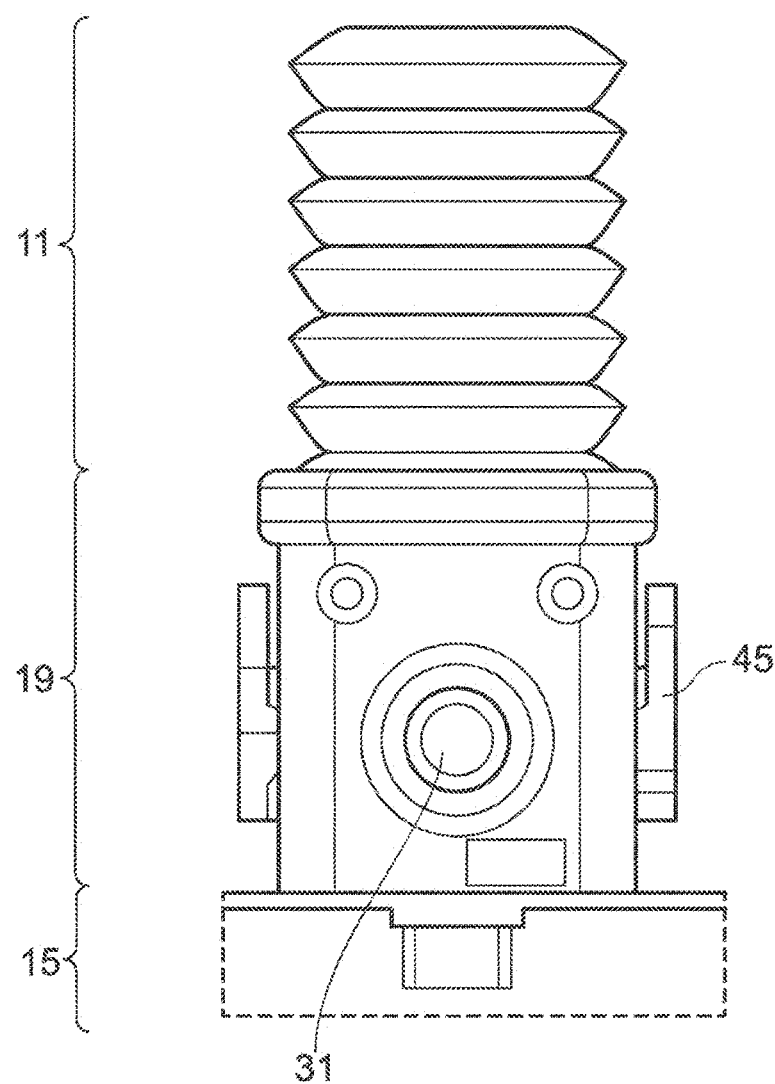
FIG. 5 illustrates an isolated side view of one auxiliary container port and auxiliary container of the cell processing device FIG. 2.

FIG. 5 depicts the filling port 31 and lever 45 mounted on the auxiliary container port 19. The lever 45 is provided in order to fill the auxiliary container 11 without allowing material to flow into the valve means 27 or primary container 13. The lever 45 is operatively connected to a 4-way stopcock that forms the connector 26 in the example described above. At the fill position (lever pointing down), the filling port 31 is opened and flow of material through the filling port 31 is directed into the auxiliary container 11. Then, at the feed position (lever pointing up), the filling port 31 is closed and flow is directed from the auxiliary container 11 via the fluid communication channel (e.g., flexible tubing 29) and into the primary container 13.

Sterile Connectors

Figure 12:
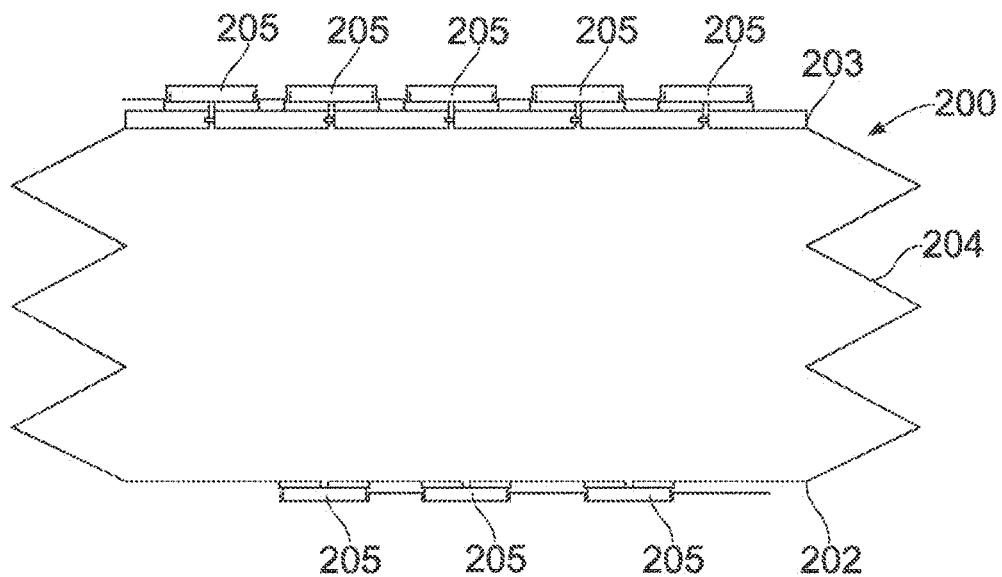
FIG. 12 shows a perspective view from the side of a representation of one embodiment of a cell processing container comprising a plurality of sterile connectors according to an embodiment of the disclosure.

FIG. 12 shows a cell processing container 200 according to an embodiment of the disclosure. Cell processing container 200 comprises a base section 202, a top section 203 and a wall element 204 arranged between the top section 203 and the base section 202. The wall element 204 is preferably composed of a flexible material. The wall element 204 is preferably compressible with respect to the top section 203 and the base section 202. The cell processing container 200 may thereby have a "concertina" or "bellows arrangement," e.g., it may have one or more z-folds in the wall element 204 arrangement.

The cell processing container 200 may comprise 1 sterile connector end and preferably comprises a plurality of connector ends 205. The connector ends 205 are preferably sterile. The sterile connector ends 205 are preferably located on the top section 203 and/or on the base section 202 of the cell processing container 200. The cell processing container 200 preferably comprises at least 1, at least 2, at least 3, at least 4, or at least 5 sterile connector ends 205. According to a preferred embodiment, the sterile connector ends 205 are embedded in the cell processing container 200. The sterile connector ends 205 enable an easy and sterile connection of auxiliary containers 11 to the cell processing container 200.

The cell processing container 200 may have any possible shape. In a preferred embodiment, the cell processing container 200 has a circular, square, rectangular, elliptical, or triangular cross section.

In a preferred embodiment, when the cell processing container 200 has a circular shape, the sterile connector ends 205 are preferably connected to the top 203 and/or base 202 sections in an essentially circular pattern. The cell processing container 200 also comprises a sterile connector end 205 in the center of the top 203 and the base 202 sections. The sterile connector ends 205 are connected to the top 203 and/or base 202 sections essentially symmetrically having essentially the same distance between the different connector ends 205. This enables an easier and possibly automated process of cell and/or gene therapy manufacturing. In an alternative embodiment, when the cell culture container 200 has a circular shape, a sterile connector end 205 is connected to the center of the top section 203 and base section 202.

Figure 13:
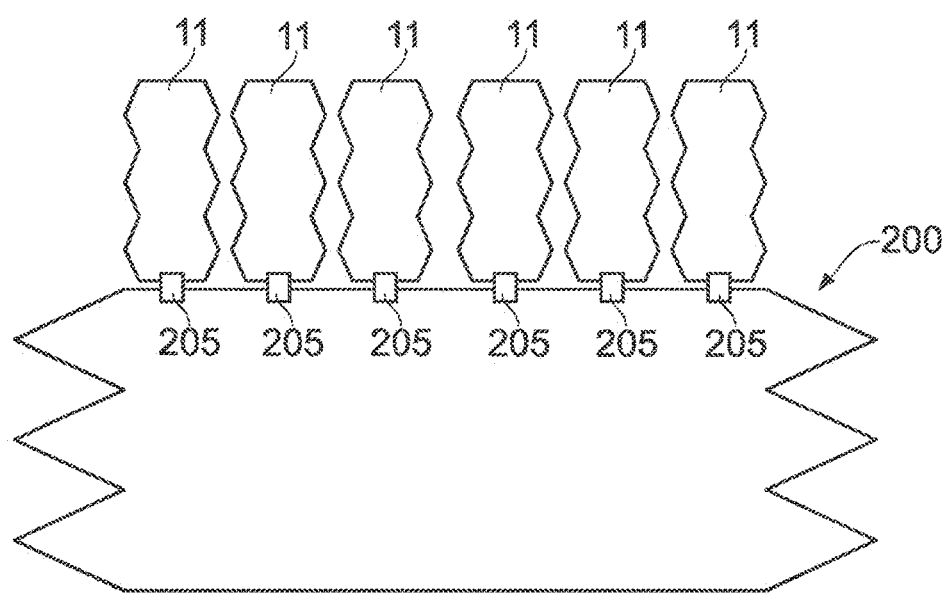
FIG. 13 shows a perspective view from the side of a representation of one embodiment of the cell processing system of the present disclosure.
Figure 14A:
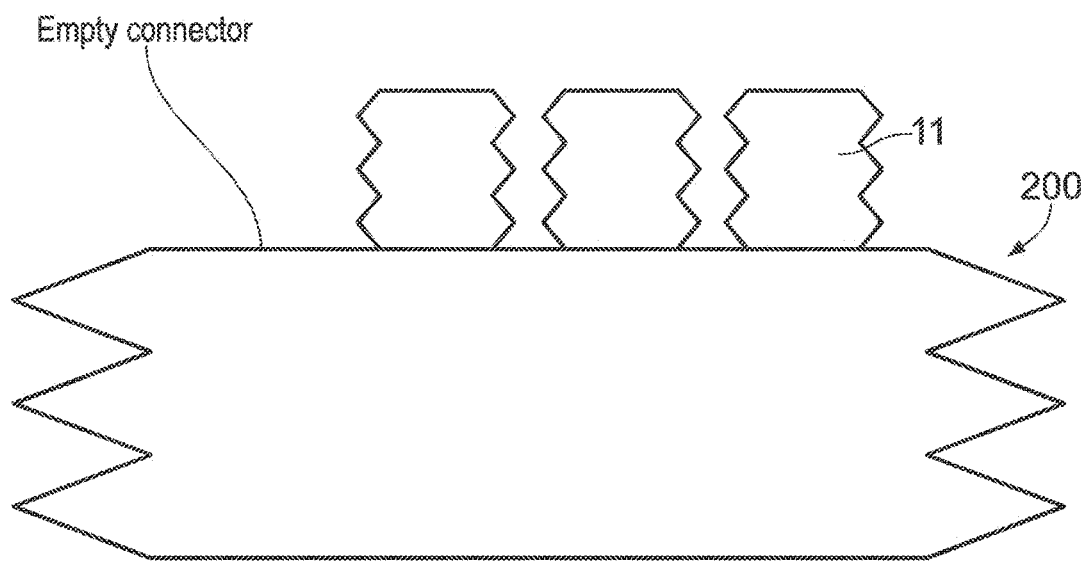
FIG. 14A shows a perspective view from the side of a representation of one embodiment of the cell processing system of the present disclosure, where auxiliary containers are connected to the cell processing container, leaving an empty auxiliary container port for a further auxiliary container to be connected.
Figure 14B:
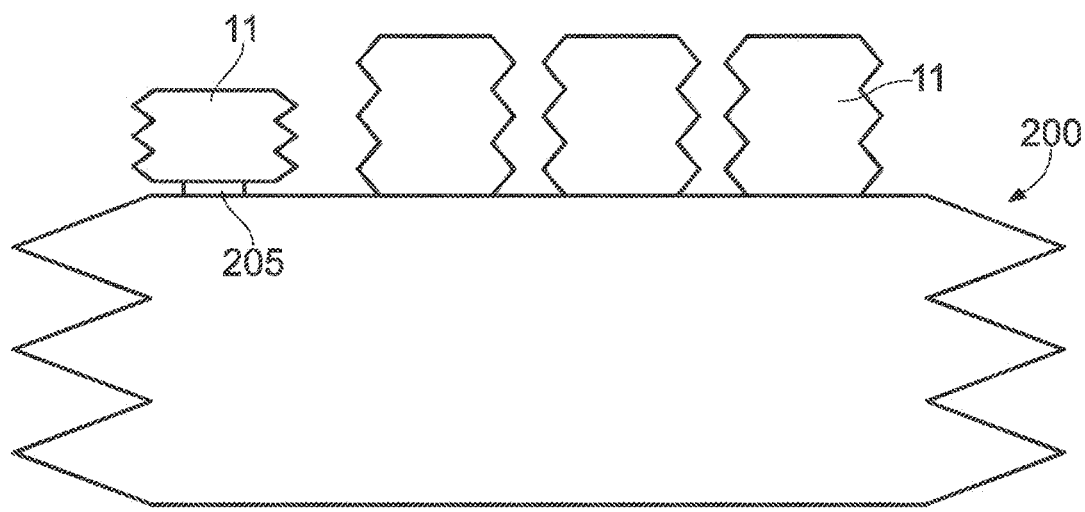
FIG. 14B shows a perspective view from the side of a representation of one embodiment of the cell processing system of the present disclosure, where an auxiliary container has been connected to the empty auxiliary container port of the cell processing container.

An embodiment of the present disclosure is shown in FIG. 13 and FIGS. 14A-14B, showing a cell processing system according to the present disclosure, comprising a cell processing container 200 as described above together with one or more auxiliary containers 11 attached to the cell processing container 200. The auxiliary containers 11 are preferably connected to the cell processing container 200 via sterile connector ends 205. The auxiliary containers 11 are preferably connected to the cell processing container 200 on the top section 203 and/or the base section 202. The auxiliary containers 11 may also be cell processing containers according to the disclosure comprising an embedded sterile connector end in a base portion of the auxiliary container 11.

In further embodiments such as the one shown in FIG. 2, the auxiliary containers 11 are fluidly coupled to the cell processing container 13 through a body portion 15. The body portion forms part of a cell processing platform 9. The auxiliary containers 11 each comprise a sterile connector end embedded in the base section of the auxiliary container 11. The embedded sterile connector end interconnects and sealingly engages with a corresponding sterile connector end in the body portion 15 of the cell processing platform 9. The cell culture container 13, being a primary container, is sealingly engaged with the bottom of the body portion 15 to form a fluid connection between the body portion 15 and the cell culture container 13.

The fluid conduit (not shown) between the sterile connector attaching the auxiliary container 11 to the body portion 15 and the fluid outlet (not shown) of the body portion 15 to which the cell processing container 13 is attached, comprises a pinch valve. The pinch valve is operable to open and close the fluid conduit in response to a valve actuator such that, as a compression force is applied to the respective auxiliary container 11, the contents of the auxiliary container can be transferred by the application of a compression force to the container. In alternative embodiments, the pinch valve may be replaced by a pressure-sensitive valve (e.g., a burst valve) such that the valve opens as a compression force is applied to the respective auxiliary container 11.

In the embodiment shown in FIGS. 14A and 14B, one or more of feed bellows 11 are pre-attached to the primary cell processing container 200 and prefilled with reagent (e.g., liquid) and stored in a refrigerator. The cell processing system shown in FIGS. 14A and 14B may be used for attaching heat labile components, such as viruses or cells, that need to be stored in at −80 degrees Celsius or in liquid nitrogen. Because, it is expensive to store the whole cell processing system at these temperatures, the embedded sterile connector ends 205 in the feed bellows 11 and in the top of the primary cell processing container 200 serve as a way to add the heat labile component(s) without use of an aseptic laminar flow hood or sterile tubing welders thus eliminating tube based connections and keeping the system compact.

Advanced blow molding techniques can be used to deposit a second (or even third), external, coating or layer of plastic impermeable to oxygen onto the wall, top and base of the auxiliary container. In this way, shelf life of the container in storage can be extended.

Figure 15A:
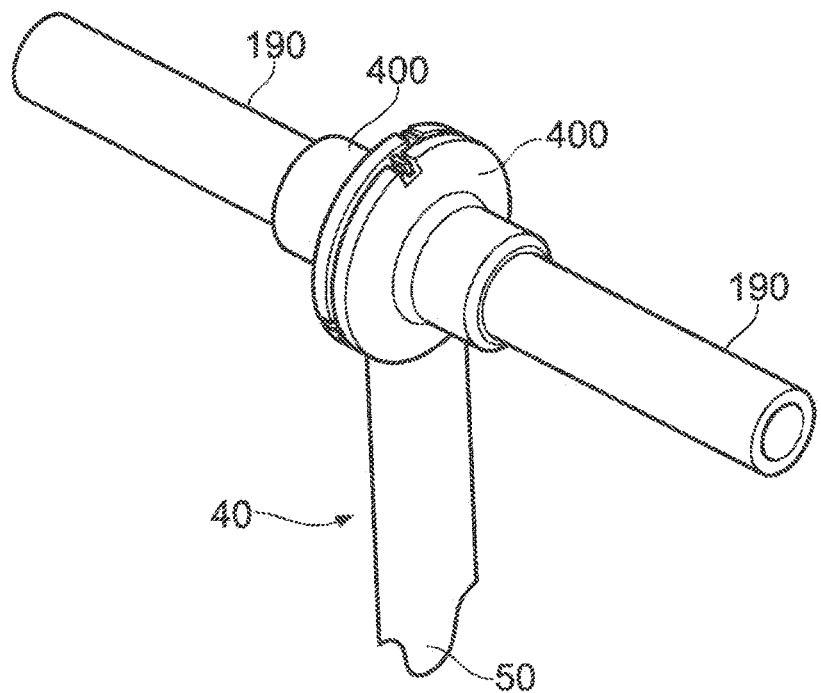
FIGS. 15A, 15B, 15C and 15D show a known sterile connector arrangement formed from two sterile connector ends.
Figure 15B:
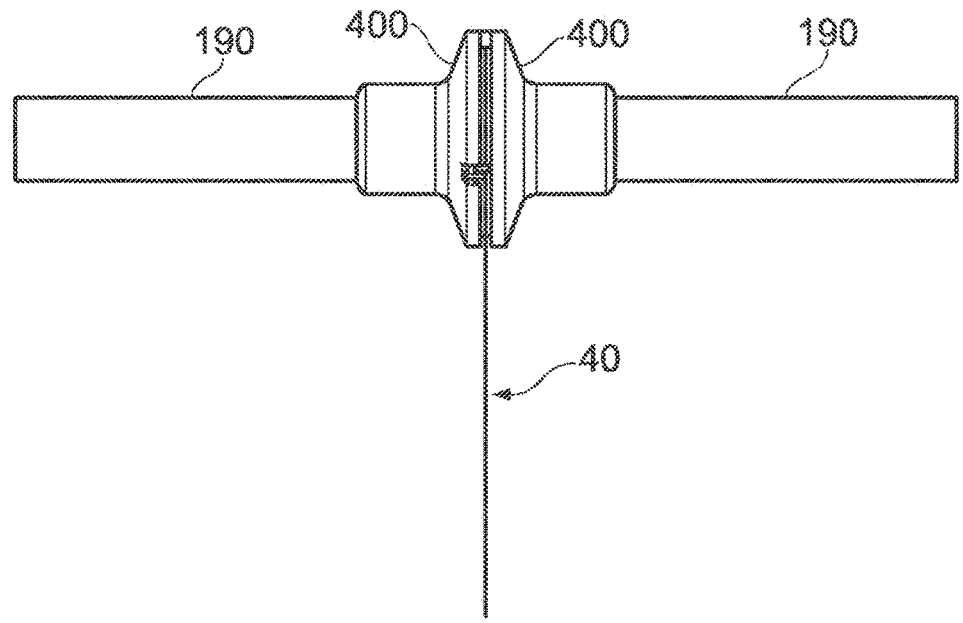
Figure 15C:
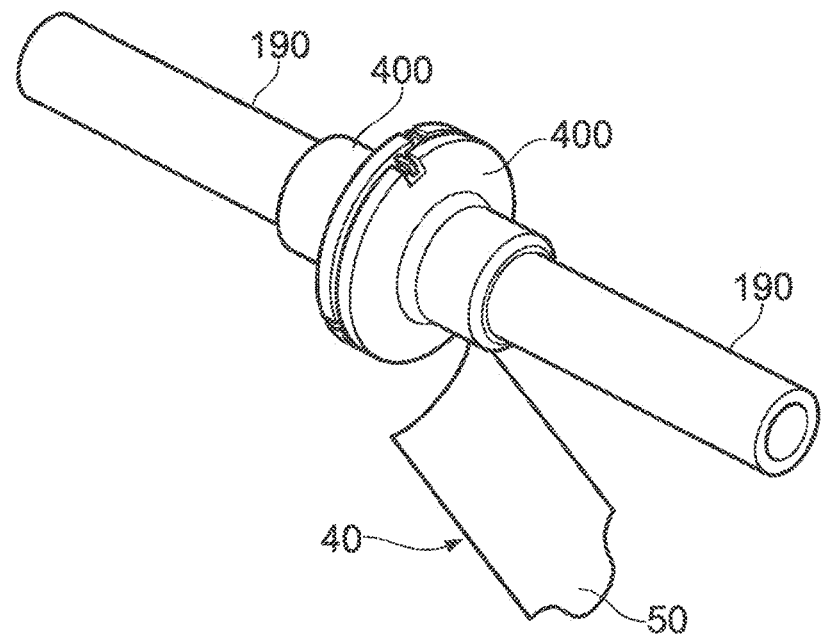
Figure 15D:
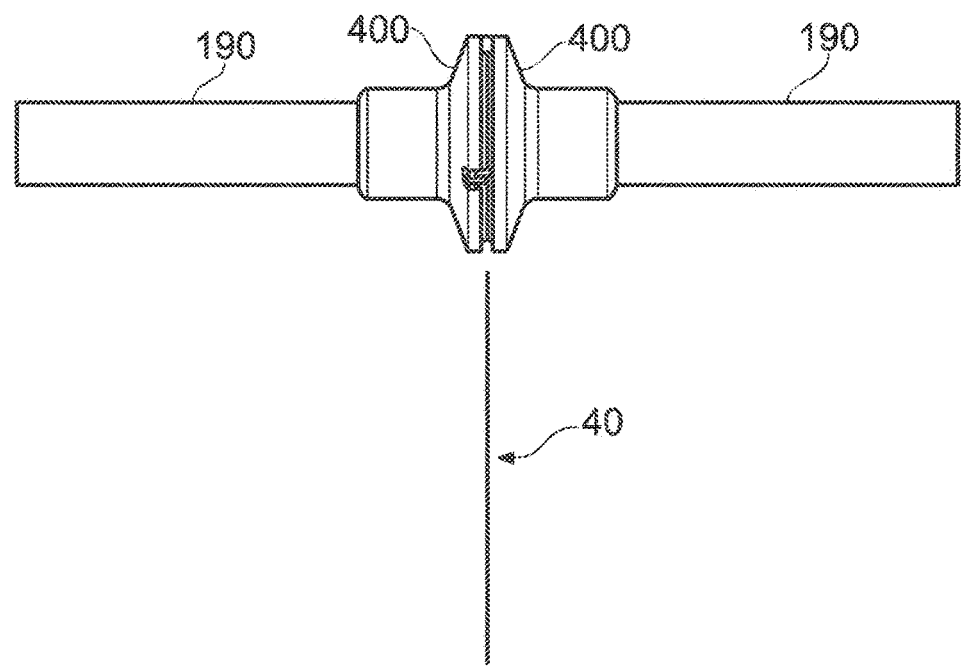

FIGS. 15A to 15D show an exemplary sterile connection between two sterile connector ends 400. The sterile connector ends 400 each have a mechanical connection (such as a screw thread) or latch (not shown) arranged in an internal circumferential manner on the sterile connector end 400. The internal circumferential latches provide the proper orientation of sterile connector end 400 relative to the other to ensure that the oppositely aligned adhesive members 40 attached to the sterile connector end 400 achieve a sterile fluid connection. In FIG. 15B, two adhesive members 40 are aligned so that the front second fold adhesive coating of each adhesive member 40 mirror each other. This alignment is important, as the rolled member 40 may be withdrawn in only one linear direction. Once the two front second fold adhesive coating surfaces are in contact, as shown in FIG. 15C, the member pull grip 50 is pulled away from the longitudinal axis of the sterile conduit 190 thereby exposing the conduit aperture (FIG. 15D). In FIGS. 15C and 15D, the rolled member 40 is completely withdrawn to an unfolded configuration and the conduit apertures are aligned to form a sterile corridor.

Figure 16A:
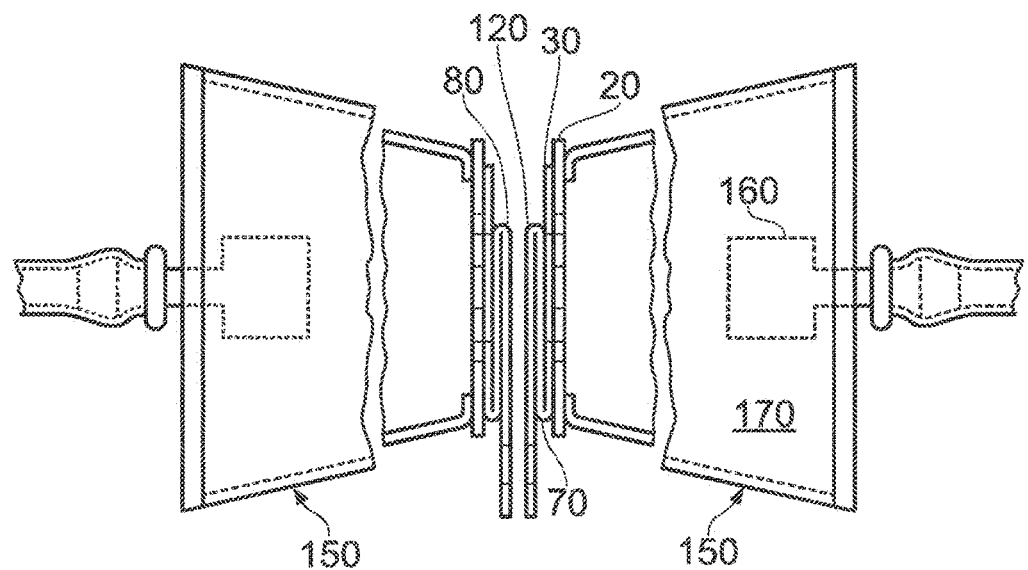
FIGS. 16A, 16B, 16C and 16D show the formation of a sterile connector from two known sterile connector ends.
Figure 16B:
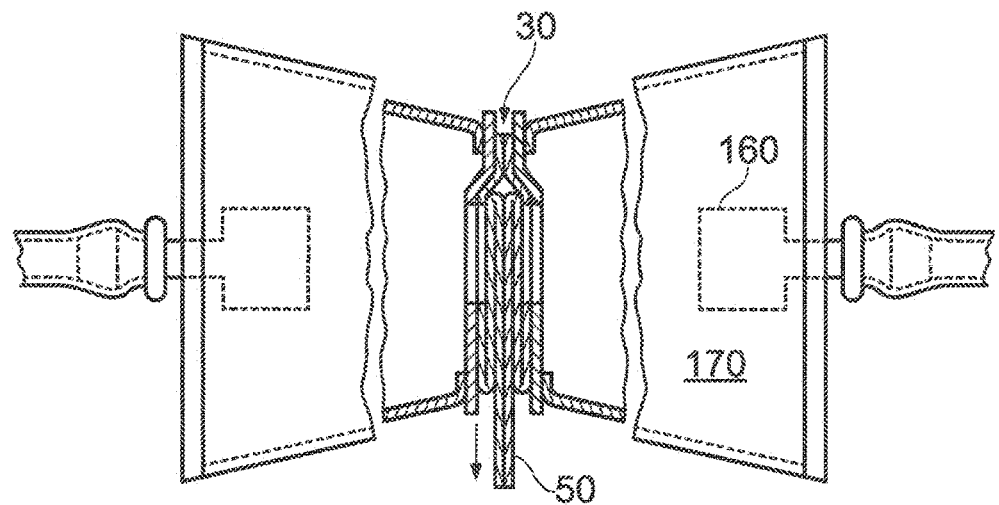
Figure 16C:
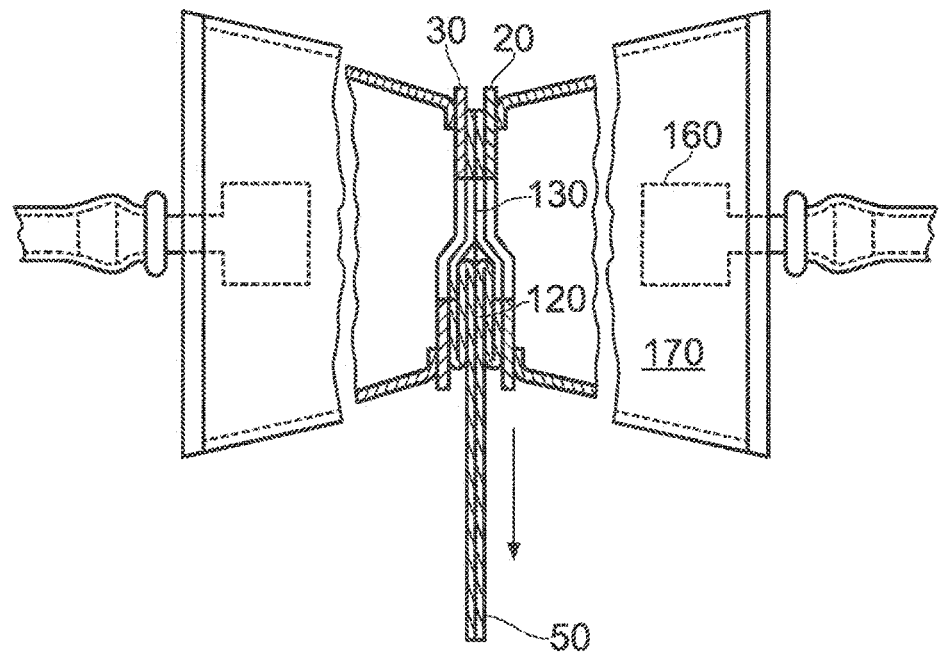
Figure 16D:
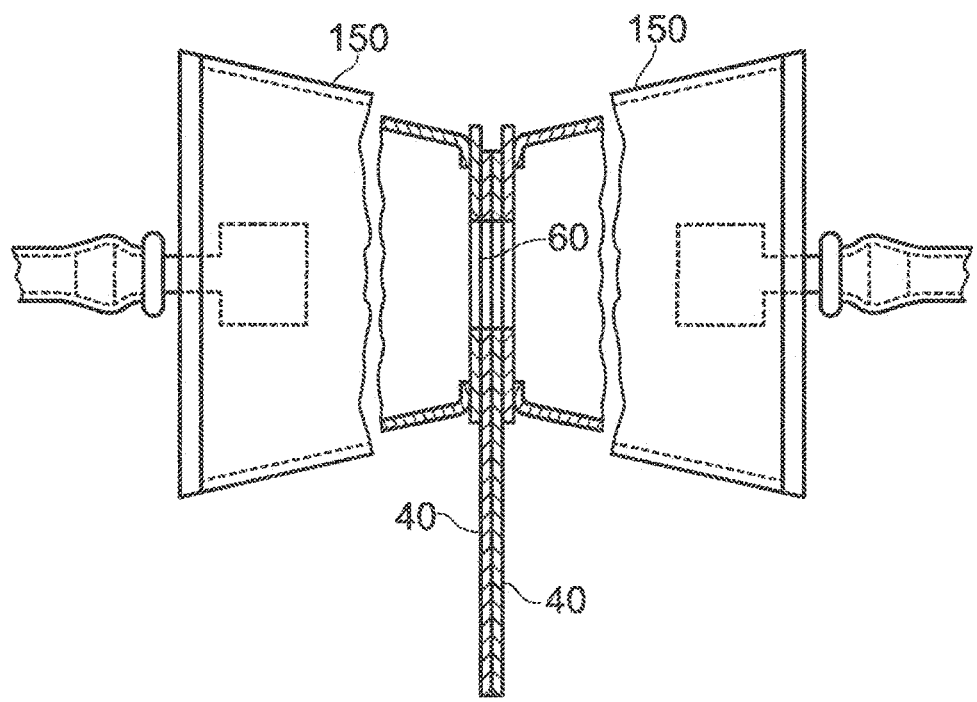

In FIG. 16A, two opposing sterile connector ends 150 are aligned so that the front second fold adhesive coating 80, 120 of each rolled membrane of the sterile connector ends 150 mirror each other. This alignment is important as the rolled membrane may be withdrawn in only one linear direction. Once the two front second fold adhesive coating 80, 120 surfaces are in contact, as shown in FIG. 16B, the entire adhesive surface areas come into contact thereby sealing each opposing sterile connector ends 150 together. In FIG. 16C, the member pull grip 50 is pulled away from the longitudinal axis of the sterile corridor thereby exposing the conduit aperture 60. In FIG. 16D, the rolled member 40 is completely withdrawn to an unfolded configuration and the conduit apertures 60 are aligned to form a sterile corridor between each sterile connector end 150.

Figure 17A:
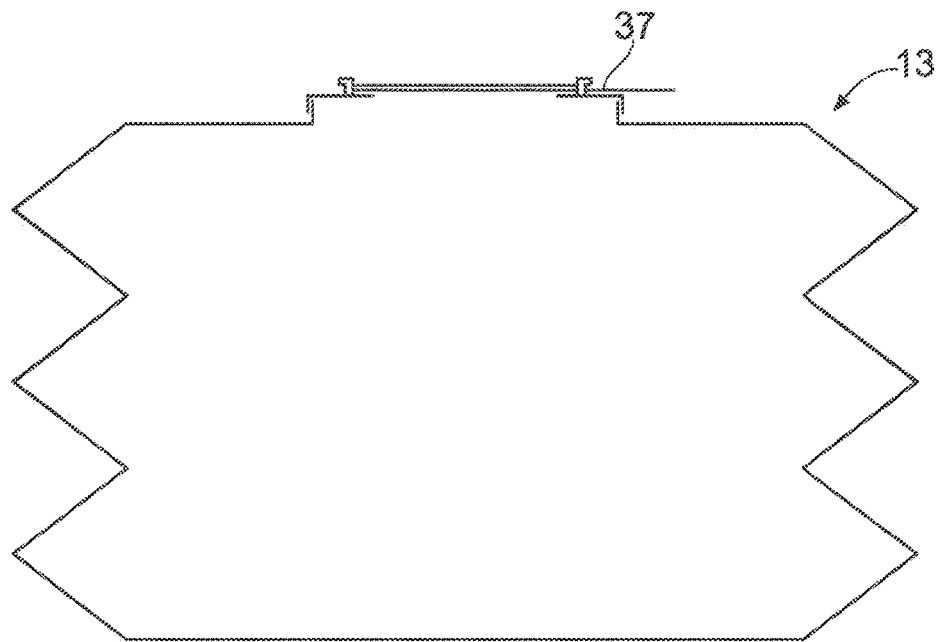
FIG. 17A shows a perspective view from the side of a representation of one embodiment of a cell processing container comprising a sterile connector end embedded therein.

FIG. 17A shows a cell processing container 13 having a sterile connector end 37 embedded in a top section of the container wall. The sterile connector end 37 forms one half of a sterile connector when the cell processing container 13 is fluidly connected to the corresponding sterile connector end in an auxiliary container 11. In alternative embodiments, the cell processing container 13 is fluidly connected to the corresponding sterile connector end in a body portion 15 of a cell processing platform 9. The sterile connector end in a body portion 15 of a cell processing platform 9 is part of a primary container port of the platform.

Figure 17B:
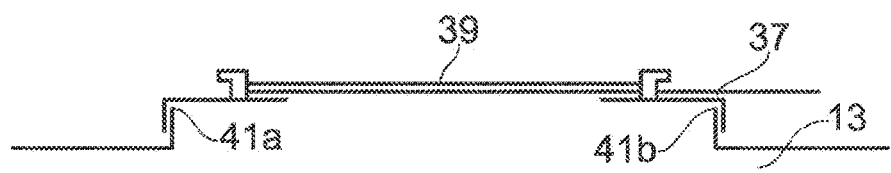
FIG. 17B shows a close view of the sterile connector end of the cell processing container of FIG. 15A.

FIG. 17B shows an exploded partial view of the sterile connector end 37 of FIG. 17A. FIG. 17B shows a male sterile connector end, being half of the sterile connector, in a top wall of cell culture container 13. The sterile connector end 37 comprises a removable paper cap 39 that, when engaged with the removable paper cap of a further sterile connector end, and is removed, exposes the sterile surfaces enclosed by a screw cap engaged with screw threads 41a and 41b of the sterile connector end 37 and creates a fluid connection through to the cell processing container lumen. Specifically, the removable paper cap is an anti-contamination pull tab that is initially folded over the sterile connector end 37 and has an end protruding therefrom. The pull tab can then be pulled out to expose the sterile surfaces to each other.

Figure 17C:
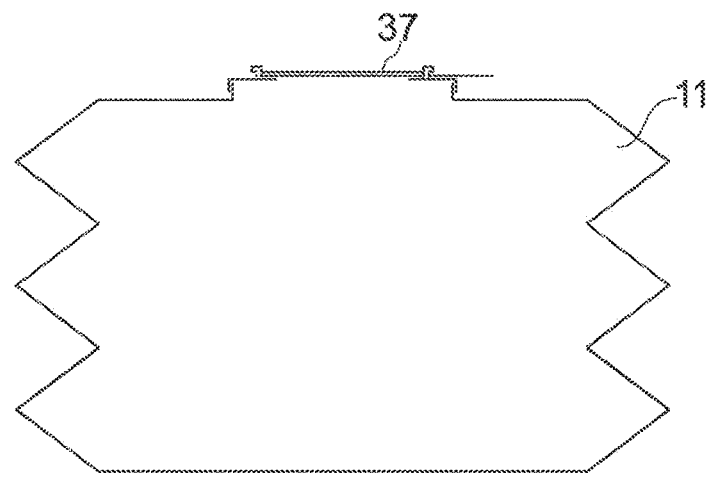
FIGS. 17C, 17D and 17E a perspective view from the side of a representation of an auxiliary container for a cell processing device and/or a cell processing system according to the disclosure comprising a sterile connector end and being prepared for filling with reagent.
Figure 17D:
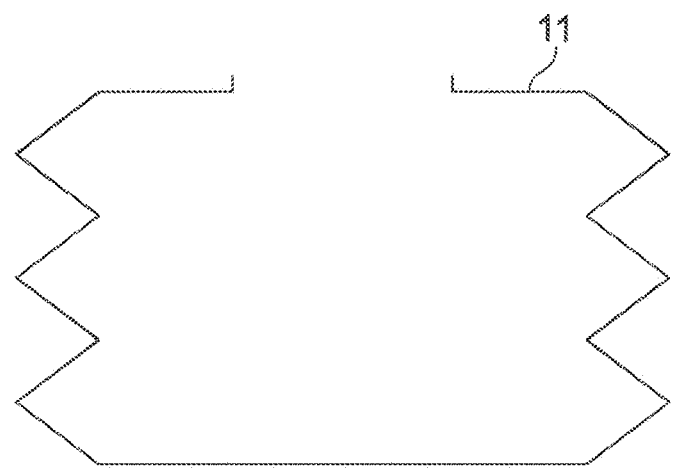
Figure 17E:
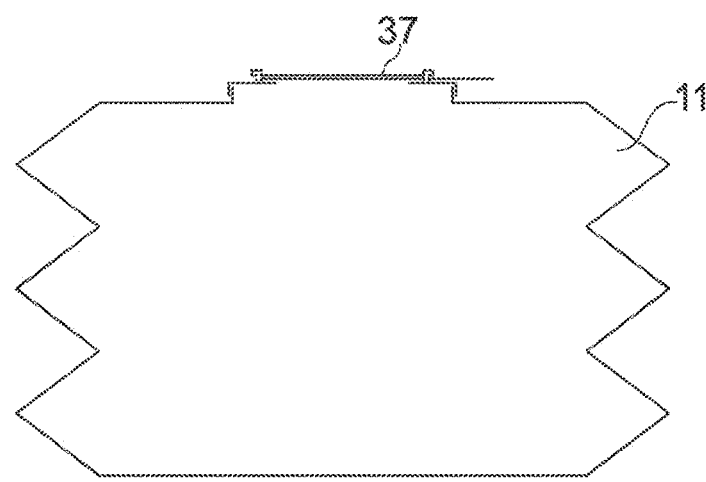

FIGS. 17C to 17E depict an auxiliary container 11 being filled with media in a sterile process. The process can be manual or automated. In FIG. 17D the sterile connector end 37 is removed and media filled into the lumen of the auxiliary container 11. The filling of the auxiliary container 11 is performed under sterile conditions. In FIG. 17E, the sterile connector end 37 is replaced and the auxiliary container 11 stored at the appropriate temperature until it is needed for assembly of the cell processing system. Once filled and ready for use, the auxiliary container 11 is inverted and the sterile connector end 37 mated and connected with a corresponding sterile connector end on a primary container such as a cell processing container.

Figure 18A:
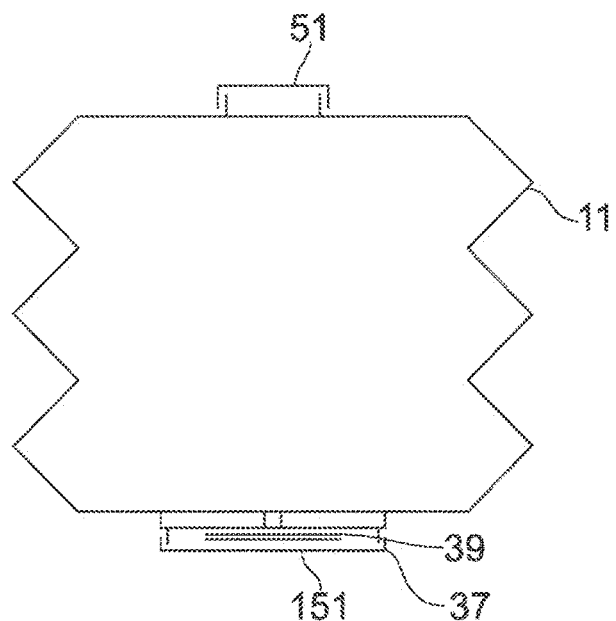
FIG. 18A shows a perspective view from the side of a representation of one embodiment of an auxiliary container comprising a sterile connector end embedded in a base section and a screw top cap in a top section.

In alternative embodiments such as the one depicted in FIG. 18A, the auxiliary container 11 has a screw cap 51 at one end and a sterile connector end 37 at the other. In this way, the integrity of the sterile connector end 37 can be maintained during storage of the auxiliary container 11 by inverting the auxiliary container 11 such that the media sits at the end of the auxiliary container 11 having the screw cap 51 and the sterile connector end 37 is free from any liquid contact.

The embedded sterile connector end 37 ensures that the auxiliary container 11 can be readily connected to an auxiliary container port of a cell processing platform 9 or directly to a cell processing container 13 in a cell processing system according to the disclosure.

FIG. 18A shows an auxiliary container 11 having a sterile connector end 37 protected by in an end cap 151 in the base section of the auxiliary container 11. The auxiliary container 11 also has a screw cap 51 in the top section of the container to allow for filling of the lumen of the container with media, or the like. The screw cap 51 is compatible with automated media filling techniques and apparatus.

The sterile connector end 37 facilitates fluid connection between the lumen of the auxiliary container and the contents in it, with a cell processing container 13 having a corresponding sterile connector end in a top section of the container 13. In order to access the sterile connector end 37 in the base section of the auxiliary container 11, the end cap 151 is removed, and the sterile connector end 37 can then be mated into sealing engagement with a corresponding sterile connector end on the cell processing container 13. In alternative embodiments, the sterile connector end 37 can be mated into sealing engagement with a corresponding sterile connector end on a cell processing platform. More specifically, the sterile connector end 37 can be mated into sealing engagement with a corresponding sterile connector end in the auxiliary container port 19 on a cell processing platform 9.

Advanced blow molding techniques can be used to deposit a second (or even third), external, coating or layer of plastic impermeable to oxygen onto the wall, top and base of the auxiliary container. In this way, shelf life of the container in storage can be extended.

Figure 18B:
FIG. 18B shows a perspective view from the side of a representation of one embodiment of a cell processing container comprising a plurality of sterile connector ends embedded in a top and a bottom section.

FIG. 18B shows a cell processing container (reactor bellow) 13 comprising a plurality of bottom sterile connectors, being embedded sterile connector ends 139, in the base section of the cell culture container 13. In the depicted embodiments, the cell processing container 13 (e.g., reactor bellow) is fitted with a plurality of sterile connector ends 141 in a top section of the container 13 for connection of a plurality of auxiliary containers 11. The auxiliary containers 11 may contain media and/or cell nutrients required for cell culture. Alternatively, the auxiliary containers may be for sampling or waste removal from cell processing container 13. In a sampling arrangement, the cell processing container (e.g., reactor bellow) 13 may be fluidly connected via a pinch valve to a removable auxiliary container 11. The pinch valve is opened and then the auxiliary container 11 is expanded to take the sample from the cell processing container 13. The pinch valve is then closed before detaching the sample auxiliary container 11. The connection could be via LUER-LOK™, or similar, that maintains a sterile barrier once the pinch valve is closed. Thus, samples may be removed from the cell processing container 13. The cell processing container 13 (e.g., reactor bellow) is fitted with a plurality of sterile connector ends 139 in a base section of the container 13 for connection to a plurality subsequent collection/processing bellows (not shown). Pinch valves 127 are housed between the sterile connector ends 141 and the cell culture container 13, which pinch valves 127 can be used to switch on/off the flow of feeds from the auxiliary containers 11. Such valve activation is useful/necessary, for example, if only partial volumes are needed or feed needs to be added from a single auxiliary container at two or more time points.

In alternative embodiments, pinch valves can be embedded in the outlet tubing from each auxiliary container 11.

In yet further alternative embodiments, the pinch valves can be pressure actuated to open when compression force is applied to the respective auxiliary container 11.

Figure 18C:
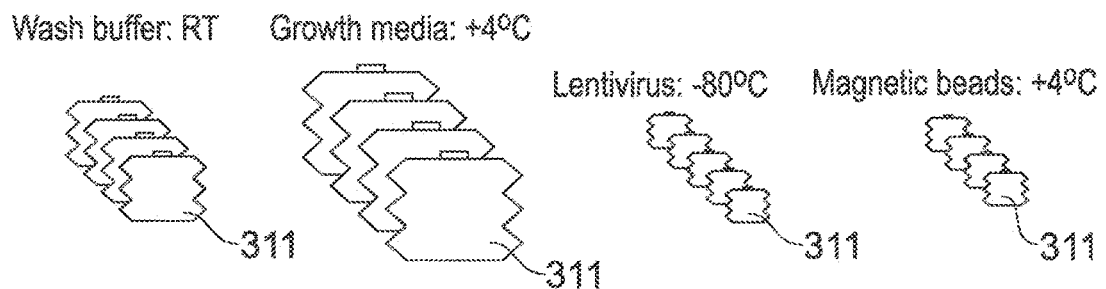
FIG. 18C shows a schematic representation of a number of prefilled auxiliary containers being connected to a cell processing container to create a cell processing system according to the disclosure having a sterile connector end in an auxiliary container port for receiving a further auxiliary container containing patient cells.
Figure 18C:
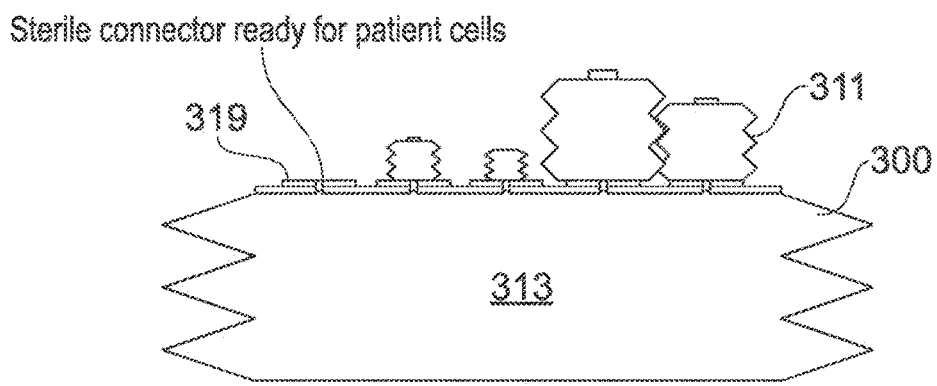

FIG. 18C shows the use of prefilled auxiliary containers 311 in a cell processing system 300 according to the disclosure. Four auxiliary containers 311 are prefilled with wash buffer and are stored at room temperature. Four further auxiliary containers 311 are prefilled with growth media and are stored at 4 degrees Celsius. Five auxiliary containers 311 are prefilled with Lentivirus are stored at −80 degrees Celsius. Four further auxiliary containers 311 are prefilled with media incorporating magnetic beads and stored at 4 degrees Celsius. One each of the prefilled auxiliary containers 311 are connected to the cell processing container 313 via sterile connector ends embedded in the base portion of each auxiliary container 311 and in the top of the cell culture container 311. An auxiliary container port 319 remains empty and ready for receiving a container including patient cells. It should be appreciated that in alternative embodiments, the cell processing system 300 comprises a different number of prefilled auxiliary containers 311 according to the present disclosure. For example, each set of prefilled auxiliary containers 311 may comprise 10s or even 100s of containers 311.

The cell processing system including the auxiliary containers 311 and the cell processing container 313 is now ready for processing in a cell processing unit according to the disclosure.

Figure 18D:
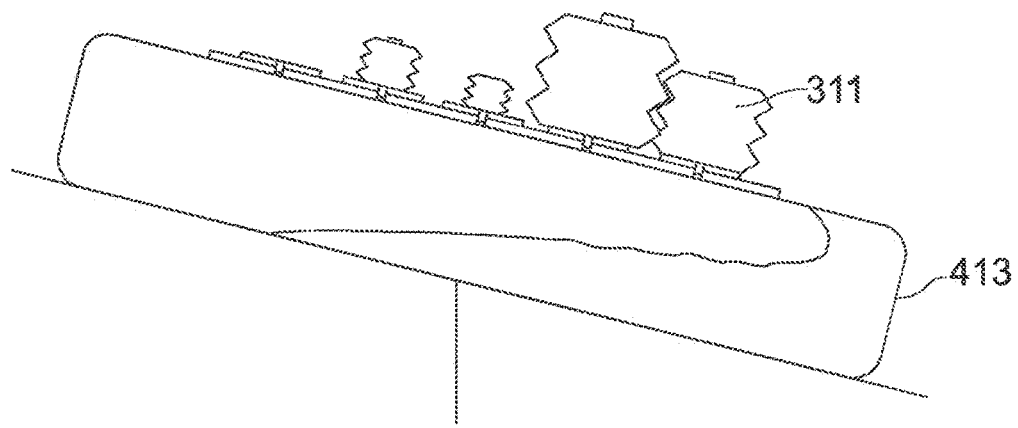
FIG. 18D shows a schematic representation of a number of prefilled auxiliary containers being connected to a single use wave container to create a cell processing system according to the disclosure having a sterile connector end in an auxiliary container port for receiving a further auxiliary container containing patient cells.
Figure 18E:
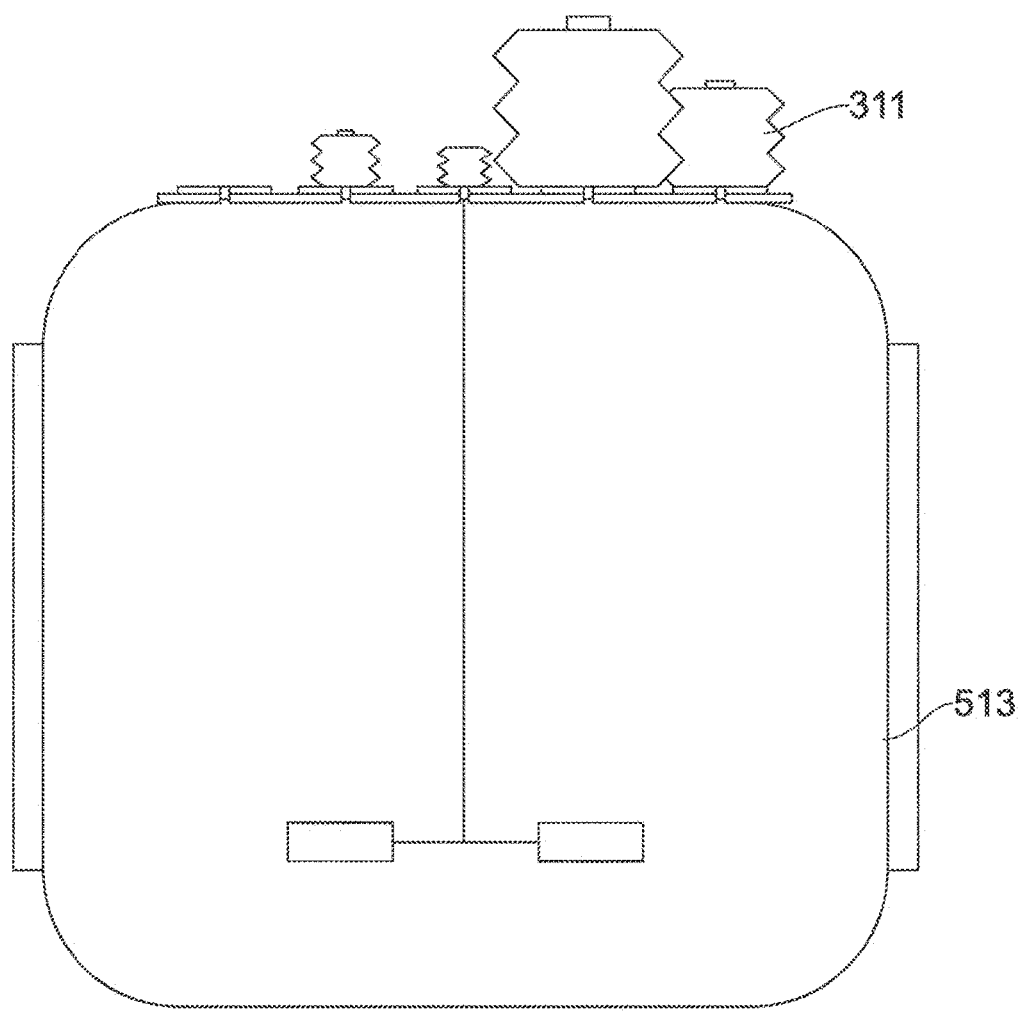
FIG. 18E shows a schematic representation of a number of prefilled auxiliary containers being connected to a CSTR bioreactor to create a cell processing system according to the disclosure having a sterile connector end in an auxiliary container port for receiving a further auxiliary container containing patient cells.

FIGS. 18D and 18E shows the prefilled auxiliary containers 311 housed on a conventional single use wave bioreactor 413 and CSTR bioreactor 513.

The cell processing unit, cell processing platform, cell processing device and cell processing container according to the disclosure may be used in any chemical, biological or separation process. Unit processes (e.g., steps) of such processes may be undertaken. The cell processing device, in conjunction with the cell processing unit and, optionally, at least one cell processing container of the disclosure may be used in cell culture processes (e.g., culturing, manipulating, expanding or storing cells) or in gene modification processes (e.g., steps including purifying, genetically modifying, recovery and wash processes). Other suitable unit processes that can be performed in the cell processing unit, platform, device and container of the disclosure include but are not limited to purification (e.g., affinity, size), washing, settling, centrifugation, filtration, chromatography, magnetic bead processes, transduction, electroporation, novel hydrogels, shipping and thawing, expansion of cells in culture, genetic modification and cryopreservation.

A cell processing device and a cell processing container of the disclosure are each suitable for cell culture and processing of cells, including the use of the container in cell therapy, gene therapy vector production and/or exosome production. A container or device of the disclosure may be suitably sterilized prior to use (e.g., by gamma irradiation or other means). Optionally the internal surface of the container may be coated with or comprise biologically active agents that can act on the cells in culture and/or induce differentiation.

The cell processing equipment described herein may be used in cell manufacturing and/or gene therapy manufacturing processes involving any suitable cell or gene type. For example, the device of the disclosure may be used to culture any prokaryotic or eukaryotic cell, suitably an animal cell, e.g., a mammalian, cell. The cells may be human or non-human. Examples of sources of suitable non-human cells include, rodents such as mice, rats, and guinea-pigs, as well as ungulate animals selected from ovine, caprine, porcine, bovine and/or equine species, or non-human primate species. However, the cells may be bacteria, yeast, fungi or plant cell in origin also.

The cells may be of any type including somatic cells and non-somatic cells. The cells may be stem cells derived from any stage of development of the embryo, fetus or adult animal. The cells may be genetically modified cells, such as chimeric antigen receptor T-cells (CARTs). The cells may be from a deposited cell line, such as genetically-modified Chinese Hamster Ovary (CHO) cells to produce recombinant proteins.

For example, embryonic stem (ES) cells, including cells of non-human origin. The cells may be derived from a deposited cell line, such as an ES cell line. The ES cells may be derived from means that do not necessitate the destruction of a human embryo such as parthenogenetic activation, as described in WO 2003/046141. The cells may be cells of a cancer or a hybridoma that can be caused to proliferate in culture and/or produce monoclonal antibodies. The cells may also be derived from the result of somatic cell nuclear transfer (SCNT) in which the nucleus of a somatic cell is placed into an enucleated oocyte.

The cells may be pluripotent stem cells, for example, primate pluripotent stem (pPS) cells, for example, human embryonic stem (hES) cells. Where the cells are stem cells, the source may be from any tissue of the body, including mesenchymal stem cells (including umbilical cord derived stem cells), neural stem cells or hematopoietic stem cells. Also included are induced pluripotent stem (iPS) cells.

The present disclosure therefore provides for the processing of cells within a single device with multiple unit processes taking place as desired within the cell processing device via delivery/extraction of desired reagents, waste, cells, or product into or from one or more auxiliary containers in fluid communication with the primary container, thereby avoiding the risk of contamination. The system is simpler to use and further avoids the complexity of existing approaches. The disclosure provides for the safer processing of cells with improved reproducibility and ease of use.

The disclosure also provides for the extraction of cells from a patient (biopsy, such as blood or bone marrow), separation of cells, processing of cells (including cytokine stimulation and/or genetic modifications), solid-liquid separations and loading into a delivery device where the cells can be cultured in the same device throughout the entire process.

In embodiments of the disclosure, cell processing containers for performing unit operations in cell and/or gene therapy manufacturing can be assembled in any configuration. In this way, a cell processing system may be provided within which a wide variety of processes (both biological, chemical and separations) can be undertaken. Similarly, the cell processing system may comprise a cell processing platform of the disclosure in conjunction with one or more cell processing containers. In this way it is possible to provide a multistage bioreactor operable to perform one or more unit operations in cell and/or gene therapy manufacturing. Because each cell processing container is based on a concertina arrangement (which can act as a pump) there is no need for pumps and complex sets of tubing/pipes. The system therefore shrinks the space needed for any given manufacturing process. A cell processing system according to the disclosure is particularly well suited for autologous (patient specific) cell and gene therapy where one needs to run a whole manufacturing run for each patient. Using traditional manufacturing approaches is not feasible when scaling up to over 5000 patients/year given the amount of space needed to run so many parallel manufacturing runs.

Certain embodiments of the disclosure are described in the following numbered clauses. In certain embodiments, unless mutually incompatible, any one or more of the features of one numbered clause may be combined with any one or more of the features of any other one or more of the numbered clauses. More specifically, any one of clauses 1 to 16 may be combined with one or more of any one of clauses 17 to 56 unless mutually incompatible. Further, any one of clauses 1 to 16 may be combined with one or more of any one of clauses 57 to 85 unless mutually incompatible. Yet further, any one of clauses 17 to 56 may be combined with one or more of any one of clauses 57 to 85 unless mutually incompatible.

In certain embodiments, unless mutually incompatible, any one or more of the following numbered clauses may be combined with any one or more of the accompanying claims.

1. A cell processing container for use in one or more unit operations in cell and/or gene therapy manufacture, the container having a base section, a top section arranged substantially in parallel with the base section and a wall element arranged between the top section and the base section and defining an internal lumen of the container, in which the wall element of the cell processing container preferably is compressible with respect to the top and base section and the wall element of the cell processing container is composed of a flexible material, wherein the cell processing container comprises at least one sterile connector end configured to operatively couple with a further sterile connector end to form a sterile connector between the cell processing container and a further component to which the cell processing container is to be fluidly connected.

2. A cell processing container according to clause 1, wherein the at least one sterile connector end is a genderless sterile connector end configured to operatively couple with a further genderless sterile connector end.

3. A cell processing container according to clause 1, wherein the at least one sterile connector end is a male sterile connector end configured to operatively couple with a female sterile connector end.

4. A cell processing container according to clause 1, wherein the at least one sterile connector end is a female sterile connector end configured to operatively couple with a male sterile connector end.

5. A cell processing container according to any one of the preceding clauses, comprising a plurality of sterile connector ends each configured to operatively couple with a separate further sterile connector end to form a plurality of sterile connectors between the cell processing container and at least one further component to which the cell processing container is to be fluidly connected.

6. A cell processing container according to any one of the preceding clauses, wherein the sterile connector ends are embedded in the cell processing container.

7. A cell processing container according to any one of the preceding clauses, wherein the sterile connector end is operatively coupled to a pinch valve embedded in the cell processing container.

8. A cell processing container according to any one of the preceding clauses, wherein the cell processing container has a circular, square, rectangular, elliptical, or triangular cross section.

9. A cell processing container according to clause 8, wherein, when the cell processing container has a circular shape, the sterile connector end(s) is/are connected to the top and/or base section of the cell processing container in an essentially circular pattern.

10. A cell processing system, comprising a cell processing container according to any one of clauses 1-9, further comprising one or more auxiliary containers detachably connected to the cell processing container.

11. A cell processing system according to clause 10, wherein one or more of the auxiliary containers comprises the further sterile connector end and is connected to the cell processing container via the further sterile connector end.

12. A cell processing system according to clause 10 or clause 11 wherein one or more of the auxiliary containers is located on the top section of the cell processing container.

13. A cell processing system according to clause 10 or clause 12, wherein one or more of the auxiliary containers is located at or near the base section of the cell processing container.

14. A cell processing system according to any one of clauses 10 to 13, wherein the one or more auxiliary containers have a base section, a top section arranged substantially in parallel with the base section and a wall element arranged between the top section and the base section and defining an internal lumen of the container, in which the wall element of the auxiliary container preferably is compressible with respect to the top and base section and the wall element of the auxiliary container is composed of a flexible material.

15. A multi-step method of performing one or more unit operations in cell and/or gene therapy manufacture using a cell processing system according to clauses 10-14.

16. The method according to clause 15, comprising introducing a cell population of interest into the cell processing container and sequentially adding one or more reagents from one or more auxiliary containers into the cell processing container in order to effect the desired one or more unit operations in cell and/or gene therapy manufacture.

17. A cell processing device for use in performing one or more unit processes in cell and/or gene therapy manufacturing, comprising a cell processing platform fluidly coupled to at least one auxiliary container and to at least one primary container, the cell processing platform comprising a body portion comprising at least one fluid inlet fluidly connected to a fluid outlet, and an auxiliary container port fluidly coupled to the at least one fluid inlet of the body portion, wherein the at least one auxiliary container is received in sealing engagement with the auxiliary container port such that the auxiliary container lumen is fluidly connected with the at least one fluid inlet of the body portion, and a primary container is received in sealingly engagement with the primary container port such that the primary container lumen is fluidly connected with the fluid outlet of the body portion.

18. A cell processing device according to clause 17, wherein the auxiliary container port comprises a container-receiving sleeve connected to the body portion and being configured to surround at least a portion of the auxiliary container, which portion comprises the fluid outlet of the container.

19. A cell processing device according to clause 17 or clause 18, wherein the cell processing platform comprises a plurality of auxiliary container ports and wherein each one of a plurality of auxiliary containers are received in sealing engagement with one of the plurality of auxiliary container ports such that the lumen of each auxiliary container is fluidly coupled with a fluid inlet of the body portion.

20. A cell processing device according to clause 19, wherein each auxiliary container port is coupled to a separate fluid inlet of the body portion.

21. A cell processing device according to clause 20, wherein each separate fluid inlet of the body portion is fluidly connected to a fluid outlet of the body portion.

22. A cell processing device according to any one of clauses 17 to 21, wherein the at least one fluid inlet and the fluid outlet of the body portion are fluidly coupled to one another by a fluid conduit.

23. A cell processing device according to clause 22, wherein the fluid conduit comprises a valve operable to open and close the fluid conduit.

24. A cell processing device according to clause 23, wherein the valve is one of: a pinch valve, a pressure-sensitive valve, a clamp valve, a membrane valve, a rupture disc, a venous valve and an aperture valve.

25. A cell processing device according to any one of clauses 17 to 24, wherein each auxiliary container port comprises a container filling port.

26. A cell processing device according to clause 25, wherein the container filling port is fluidly connected to a fluid inlet of the auxiliary container port.

27. A cell processing device according to clause 25 or clause 26, wherein each container filling port comprises a valve operatively coupled to the fluid inlet and a fluid outlet of the auxiliary container port and operable to control fluid flow direction through the auxiliary container port.

28. A cell processing device according to any one of clauses 25 to 27, wherein the container filling port comprises a valve operable, in an open position, to allow fluid to flow to the fluid inlet of the auxiliary container port and not to the fluid outlet of the auxiliary container port and, in a closed position, to close the container filling port and to allow fluid to flow from the fluid inlet of the auxiliary container port to the fluid outlet of the auxiliary container port.

29. A cell processing device according to any one of clauses 17 to 28, wherein the at least one auxiliary container comprises a mating element configured to fluidly connect to a corresponding mating element on the auxiliary container port.

30. A cell processing device according to clause 29, wherein the mating element is at least one of: a sterile connector end or a LUER-LOK™.

31. A cell processing device according to any one of clauses 17 to 30, wherein the primary container port comprises a mating element configured to fluidly connect to a corresponding mating element on the primary container.

32. A cell processing device according to clause 31, wherein the mating element comprises at least one of: a sterile connector end or a LUER-LOK™.

33. A cell processing device according to any one of clauses 17 to 32, wherein the auxiliary container port comprises a sterile connector end at the fluid inlet and/or the fluid outlet of the auxiliary container port, each sterile connector end configured to engage with a further sterile connector end on a container and/or on the body portion, respectively.

34. A cell processing device according to any one of clauses 17 to 33, wherein the fluid outlet of the body portion comprises a sterile connector end configured to engage with a further sterile connector end on the primary container attachable to the body portion.

35. A cell processing device according to any one of clauses 17 to 34, comprising at least one positional tracking device operable to indicate a set location on the platform.

36. A cell processing device according to clause 35, wherein the positional tracking device is one or more of: a magnet, an RFID sensor, a light sensor or a cog operable to engage a further cog.

37. A cell processing device according to clause 35 or clause 36, comprising a plurality of positional tracking devices.

38. A cell processing device according to any one of clauses 35 to 37, wherein the at least one positional tracking device is located relative to the auxiliary container port such that the location of the positional tracking device is related to the position of the auxiliary container port.

39. A cell processing device according to any one of clauses 35 to 38, wherein the at least one positional tracking device is located on the body portion relative to the auxiliary container port.

40. A cell processing device according to any one of clauses 35 to 39, comprising a plurality of positional tracking devices each located on the body portion relative to an auxiliary container port.

41. A cell processing device according to any one of clauses 17 to 40, comprising a sampling port in the body portion.

42. A cell processing device according to any one of clauses 17 to 41, comprising a gas transfer port in the body portion.

43. A cell processing device according to any one of clauses 17 to 42, wherein the auxiliary container port is configured to receive an auxiliary container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

44. A cell processing device according to any one of clauses 17 to 43, wherein the primary container port is configured to receive a primary container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

45. A cell processing device according to clause 44, wherein the primary container further comprises an attachment flange mounted to the top section of the primary container and being configured to sealingly engage and mount to the primary container port.

46. A cell processing device according to any one of clauses 17 to 45, wherein, the at least one auxiliary container is compressible.

47. A cell processing device according to any one of clauses 17 to 46, wherein the at least one auxiliary container is one of: a syringe or any shaped container with a moving seal allowing variable volume operations.

48. A cell processing device according to any one of clauses 17 to 47 wherein the at least one auxiliary container is a bag retained in a frame and moveable with respect to the frame.

49. A cell processing device according to any one of clauses 17 to 48, comprising one or more auxiliary containers detachably connected to an auxiliary container port of the cell processing platform.

50. A cell processing device according to clause 49, wherein one or more of the auxiliary containers are connected to a respective auxiliary container port with a sterile connector.

51. A cell processing device according to any one of clauses 17 to 50, wherein the at least one auxiliary container is located on the top of the cell processing platform.

52. A cell processing device according to any one of clauses 17 to 51, wherein the primary container is located on the bottom of the cell processing platform.

53. A cell processing device according to any one of clauses 17 to 52, wherein the auxiliary container is one of: a reagent container, a cell culture container, a waste container, a filter, an electroporator, a purifier, a waste container, a filter, an electroporator, a purifier, holding container, apheresis/leukopheresis, differentiation chamber, chromatography column, settling chamber, sieve, shaking/mixer, a centrifuge and a magnetic bead separator or a bioreactor.

54. A cell processing device according to any one of clauses 17 to 53, wherein the primary container is a reagent container, a bioreactor, a cell culture container, a waste container, a filter, an electroporator, a purifier, a waste container, a filter, an electroporator, a purifier, holding container, apheresis/leukopheresis, differentiation chamber, chromatography column, settling chamber, sieve, shaking/mixer, a centrifuge and a magnetic bead separator or the like, a centrifuge and a magnetic bead separator or the like.

55. A multi-step method of performing one or more unit operations in cell and/or gene therapy manufacture using a cell processing device according to clauses 17 to 54.

56. The method according to clause 55, comprising introducing a cell population of interest into the primary container and sequentially adding one or more reagents from one or more auxiliary containers into the primary container in order to effect the desired one or more unit operations in cell and/or gene therapy manufacture.

57. A cell processing platform for use in one or more unit operations in cell and/or gene therapy manufacture, the platform comprising a body portion comprising at least one fluid inlet fluidly connected to a fluid outlet, and an auxiliary container port fluidly coupled to the at least one fluid inlet of the body portion, wherein the auxiliary container port is configured and arranged to receive and sealingly engage with an auxiliary container and to fluidly connect the auxiliary container lumen with the at least one fluid inlet of the body portion, and a primary container port configured and arranged to sealingly engage with a primary container and to fluidly connect the primary container lumen with the fluid outlet of the body portion.

58. A cell processing platform according to clause 57, wherein the auxiliary container port comprises a container-receiving sleeve connected to the body portion and being configured to surround at least a portion of the auxiliary container, which portion comprises the fluid outlet of the container.

59. A cell processing platform according to clause 57 or clause 58, wherein the auxiliary container port comprises a mating element configured to fluidly connect to a corresponding mating element on an auxiliary container.

60. A cell processing platform according to clause 59, wherein the mating element is at least one of: a sterile connector end or a LUER-LOK™.

61. A cell processing platform according to any one of clauses 57 to 60, wherein the primary container port comprises a mating element configured to fluidly connect to a corresponding mating element on a primary container.

62. A cell processing platform according to clause 61, wherein the mating element comprises at least one of: a sterile connector end or a LUER-LOK™.

63. A cell processing platform according to any one of clauses 57 to 62, wherein the auxiliary container port comprises a sterile connector end at the fluid inlet and/or the fluid outlet of the auxiliary container port, each sterile connector end configured to engage with a further sterile connector end on a container and/or on the body portion, respectively.

64. A cell processing platform according to any one of clauses 57 to 63, wherein the fluid outlet of the body portion comprises a sterile connector end configured to engage with a further sterile connector end on a primary container attachable to the body portion.

65. A cell processing platform according to any of clauses 57 to 64, wherein the body portion is substantially hollow.

66. A cell processing platform according to any one of clauses 57 to 65, wherein the at least one fluid inlet and the fluid outlet of the body portion are fluidly coupled to one another by a fluid conduit.

67. A cell processing platform according to clause 66, wherein the fluid conduit comprises a valve operable to open and close the fluid conduit.

68. A cell processing platform according to clause 67, wherein the valve is one of: a pinch valve, a pressure-sensitive valve, a clamp valve, a membrane valve, a rupture disc, a venous valve and an aperture valve.

69. A cell processing platform according to any one of clauses 57 to 68, wherein the auxiliary container port comprises a container filling port.

70. A cell processing platform according to clause 69, wherein the container filling port is fluidly connected to a fluid inlet of the auxiliary container port.

71. A cell processing platform according to clause 69 or clause 70, wherein the container filling port comprises a valve operatively coupled to the fluid inlet and a fluid outlet of the auxiliary container port and operable to control fluid flow direction through the auxiliary container port.

72. A cell processing platform according to any one of clauses 69 to 71, wherein the container filling port comprises a valve operable, in an open position, to allow fluid to flow to the fluid inlet of the auxiliary container port and not to the fluid outlet of the auxiliary container port and, in a closed position, to close the container filling port and to allow fluid to flow from the fluid inlet of the auxiliary container port to the fluid outlet of the auxiliary container port.

73. A cell processing platform according to any one of clauses 57 to 72, comprising a plurality of auxiliary container ports each configured and arranged to receive and sealingly engage with an auxiliary container and to fluidly connect the container lumen with a fluid inlet of the body portion.

74. A cell processing platform according to clause 73, wherein each auxiliary container port is coupled to a separate fluid inlet of the body portion.

75. A cell processing platform according to clause 74, wherein each separate fluid inlet of the body portion is fluidly connected to a fluid outlet of the body portion.

76. A cell processing platform according to any one of clauses 57 to 75, comprising at least one positional tracking device operable to indicate a set location on the platform.

77. A cell processing platform according to clause 76, wherein the positional tracking device is at least one of: a magnet, an RFID sensor, a light sensor or a cog operable to engage a further cog.

78. A cell processing platform according to clause 76 or clause 77, comprising a plurality of positional tracking devices.

79. A cell processing platform according to any one of clauses 76 to 78, wherein the at least one positional tracking device is located relative to the auxiliary container port such that the location of the positional tracking device is related to the position of the auxiliary container port.

80. A cell processing platform according to any one of clauses 76 to 79, wherein the at least one positional tracking device is located on the body portion relative to the auxiliary container port.

81. A cell processing platform according to any one of clauses 57 to 80, comprising a sampling port in the body portion.

82. A cell processing platform according to any one of clauses 57 to 81, comprising a gas transfer port in the body portion.

83 A cell processing platform according to any one of clauses 57 to 82, wherein the auxiliary container port is configured to receive a container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

84. A cell processing platform according to any one of clauses 57 to 83, wherein the primary container port is configured to receive a primary container having a base section, a top section arranged substantially in parallel with the base section and a wall element arranged between the top section and the base section and defining an internal lumen of the container, in which the wall element of the container preferably is compressible with respect to the top and base section and the wall element of the container is composed of a flexible material.

85. A cell processing platform according to clause 84, wherein the primary container further comprises an attachment flange mounted to the top section of the primary container and being configured to sealingly engage and detachably mount to the primary container port.

The invention claimed is:

1. A cell processing unit for cell and gene therapy manufacture, comprising;
   a housing defining an enclosure into which a cell processing platform is mountable;
   a platform mounting bracket within the housing and configured and arranged to receive and retain the cell processing platform with one or more auxiliary containers and a primary container mounted to the cell processing platform;
   a primary actuator configured and arranged to exert a force on the primary container mounted to the cell processing platform;
   a rotational drive apparatus configured and arranged to operatively engage and act upon the cell processing platform to rotate the cell processing platform with respect to the platform mounting bracket; and
   an auxiliary actuator configured and arranged to exert a force on an auxiliary container mounted to the cell processing platform to expel a contents from the auxiliary container.

2. The cell processing unit of claim 1, wherein the platform mounting bracket comprises a mounting plate.

3. The cell processing unit of claim 2, wherein the platform mounting bracket comprises a mounting flange spaced apart from the mounting plate to receive and retain the cell processing platform in a position in the housing between the mounting plate and the mounting flange.

4. The cell processing unit of claim 2, wherein the mounting plate is substantially C-shaped.

5. The cell processing unit of claim 1, wherein the rotational drive apparatus comprises a drive wheel that is mounted on the platform mounting bracket and is configured to engage a surface of the cell processing platform and to impart rotational movement on the cell processing platform.

6. The cell processing unit of claim 5, wherein the rotational drive apparatus comprises a sprung wheel biased toward the drive wheel and spaced apart from the drive wheel and mounted on the platform mounting bracket.

7. The cell processing unit of claim 5, wherein the rotational drive apparatus comprises a hinged wheel biased toward the drive wheel and spaced apart from the drive wheel and mounted on the platform mounting bracket.

8. The cell processing unit of claim 7, wherein the hinged wheel is moveable into an open position in which the cell processing platform is insertable and engageable with the cell processing platform mounting bracket, and wherein the hinged wheel is moveable into a closed position in which the hinged wheel is engaged with the surface of the cell processing platform to retain the cell processing platform in the cell processing platform mounting bracket.

9. The cell processing unit of claim 1, wherein at least one of the auxiliary actuator and the primary actuator is a linear actuator.

10. The cell processing unit of claim 9, wherein the linear actuator comprises a plunger operatively coupled to a drive motor, wherein the plunger is configured to engage the auxiliary container mounted to the cell processing platform and to exert a compression force on the auxiliary container.

11. The cell processing unit of claim 1, wherein the primary actuator is configured to expel a fluid from the primary container.

12. The cell processing unit of claim 1, wherein:
   the cell processing platform includes a base plate, the auxiliary container, and the primary container, the auxiliary container and the primary container being positioned at opposite ends of the base plate;
   the platform mounting bracket includes an opening formed therein, the opening extending from a side thereof for receiving the base plate;
   the primary actuator is positioned below the opening formed in platform mounting bracket; and
   the auxiliary actuator is positioned above the opening of the platform mounting bracket.

13. The cell processing unit of claim 12, wherein the primary actuator comprises a plunger operatively coupled to a drive motor, wherein the plunger is configured to engage the primary container mounted to the cell processing platform and to exert a compression force on the primary container.

14. The cell processing unit of claim 1, comprising a location detecting sensor operable to detect a position of the cell processing platform relative to the platform mounting bracket.

15. The cell processing unit of claim 1, comprising a location detecting sensor operable to detect a rotational position of the cell processing platform relative to the platform mounting bracket.

16. The cell processing unit of claim 1, wherein one or more of the primary container and the one or more auxiliary containers mounted to the cell processing platform is compressible.

17. The cell processing unit of claim 1, wherein one or more of the primary container and the one or more auxiliary containers mounted to the cell processing platform respectively comprises: a base section, a top section arranged substantially in parallel with the base section and a wall element arranged between the top section and the base section and defining an internal lumen of the container, wherein the wall element is compressible with respect to the top and base section and the wall element comprises a flexible material.

18. The cell processing unit of claim 1, the container mounted to the cell processing unit is one of: a reagent container, a bioreactor, a cell culture container, a waste container, a filter, an electroporator, a purifier, holding container, apheresis/leukopheresis, differentiation chamber, chromatography column, settling chamber, sieve, shaking/mixer, a centrifuge or a magnetic bead separator.

19. The cell processing unit of claim 1, wherein control of the cell processing unit is automated.

20. A cell processing unit for cell and gene therapy manufacture, comprising;
    a housing defining an enclosure into which a cell processing platform is mountable;
    a platform mounting bracket within the housing and configured and arranged to receive and retain the cell processing platform;
    a rotational drive apparatus configured and arranged to operatively engage and act upon the cell processing platform to rotate the cell processing platform with respect to the platform mounting bracket, the rotational drive apparatus comprising:
        a drive wheel that is mounted on the platform mounting bracket and is configured to engage a surface of the cell processing platform and to impart rotational movement on the cell processing platform; and
        a hinged wheel biased toward the drive wheel and spaced apart from the drive wheel and mounted on the platform mounting bracket; and
    an actuator configured and arranged to exert a force on a container mounted to the cell processing platform to expel a contents from the container.

* * * * *